(12) United States Patent
Khan

(10) Patent No.: US 10,972,884 B2
(45) Date of Patent: Apr. 6, 2021

(54) RULES-BASED RIDE SECURITY

(71) Applicant: Zemcar, Inc., Bedford, MA (US)

(72) Inventor: Bilal W. Khan, Bedford, MA (US)

(73) Assignee: Zemcar, Inc., Bedford, MA (US)

( * ) Notice: Subject to any disclaimer, the term of this patent is extended or adjusted under 35 U.S.C. 154(b) by 0 days.

(21) Appl. No.: 15/337,808

(22) Filed: Oct. 28, 2016

(65) Prior Publication Data

US 2017/0127215 A1     May 4, 2017

Related U.S. Application Data

(60) Provisional application No. 62/248,687, filed on Oct. 30, 2015.

(51) Int. Cl.

| | | |
|---|---|---|
| *H04W 4/50* | (2018.01) | |
| *H04W 4/021* | (2018.01) | |
| *A61B 5/1172* | (2016.01) | |
| *G01C 21/34* | (2006.01) | |
| *G08G 1/00* | (2006.01) | |
| *H04W 12/08* | (2021.01) | |
| *H04W 12/61* | (2021.01) | |
| *H04W 12/63* | (2021.01) | |

(52) U.S. Cl.
CPC ............ *H04W 4/50* (2018.02); *A61B 5/1172* (2013.01); *G01C 21/3438* (2013.01); *G08G 1/202* (2013.01); *H04W 4/021* (2013.01); *H04W 12/08* (2013.01); *H04W 12/61* (2021.01); *H04W 12/63* (2021.01)

(58) Field of Classification Search
None
See application file for complete search history.

(56) References Cited

U.S. PATENT DOCUMENTS

| | | | |
|---|---|---|---|
| 10,325,228 B2 | 6/2019 | Khan | |
| 2005/0075119 A1* | 4/2005 | Sheha | G01C 21/26 455/456.6 |
| 2006/0055779 A1* | 3/2006 | Li | B60R 1/008 348/148 |
| 2006/0276960 A1 | 12/2006 | Adamczyk et al. | |
| 2007/0273762 A1* | 11/2007 | Steensma | G08B 13/19663 348/143 |
| 2008/0270019 A1 | 10/2008 | Anderson et al. | |
| 2008/0277183 A1 | 11/2008 | Huang et al. | |
| 2009/0009321 A1* | 1/2009 | McClellan | G08G 1/207 340/539.13 |
| 2010/0279627 A1* | 11/2010 | Bradley | H04W 48/04 455/69 |
| 2011/0059693 A1 | 3/2011 | O'Sullivan | |

(Continued)

OTHER PUBLICATIONS

International Search Report and Written Opinion for corresponding PCT Appl No. PCT/US2016/059474, dated Feb. 17, 2017.

(Continued)

*Primary Examiner* — Tonya Joseph
(74) *Attorney, Agent, or Firm* — Fish & Richardson P.C.

(57) ABSTRACT

A method includes receiving, through the user interface of a user device of a user, a request for a ride from the user; assigning a driver to provide the ride for the user; according to one or more application rules associated with the request for the ride, providing the driver with access to information uniquely identifying the user or a rider.

20 Claims, 24 Drawing Sheets

(56) References Cited

U.S. PATENT DOCUMENTS

| | | |
|---|---|---|
| 2012/0203599 A1 | 8/2012 | Choi et al. |
| 2012/0290652 A1 | 11/2012 | Boskovic |
| 2013/0091540 A1 | 4/2013 | Chen et al. |
| 2013/0138484 A1* | 5/2013 | Wu ............... G06Q 30/0212 705/13 |
| 2013/0246207 A1 | 9/2013 | Novak |
| 2013/0246301 A1 | 9/2013 | Radhakrishnan |
| 2014/0082069 A1* | 3/2014 | Varoglu ............ G06Q 50/01 709/204 |
| 2014/0129302 A1* | 5/2014 | Amin ............ G06Q 30/0641 705/13 |
| 2014/0129951 A1 | 5/2014 | Amin |
| 2014/0309863 A1* | 10/2014 | Ricci ............. G01C 21/3484 701/36 |
| 2014/0375800 A1* | 12/2014 | Lim ............. H04M 1/72538 348/143 |
| 2015/0024705 A1* | 1/2015 | Rashidi ............. H04W 4/90 455/404.2 |
| 2015/0141060 A1* | 5/2015 | Shan ................ H04W 4/21 455/456.3 |
| 2015/0161564 A1 | 6/2015 | Sweeney et al. |
| 2015/0161752 A1* | 6/2015 | Barreto ............. G06Q 50/30 705/7.15 |
| 2015/0204684 A1 | 7/2015 | Rostamian et al. |
| 2015/0356703 A1 | 12/2015 | Ellis |
| 2016/0110836 A1 | 4/2016 | Garg |
| 2016/0283994 A1 | 9/2016 | Edgington et al. |
| 2016/0300242 A1 | 10/2016 | Truong |
| 2016/0300318 A1 | 10/2016 | Godil |
| 2016/0363458 A1 | 10/2016 | Guo |
| 2017/0124506 A1 | 5/2017 | Khan |

OTHER PUBLICATIONS

International Search Report and Written Opinion for corresponding PCT Appl No. PCT/US2016/059448, dated Jan. 24, 2017.
Extended European Search Report for Application No. EP 16 86 0931, dated May 29, 2019, 7 pages.
Extended European Search Report for Application No. EP 16 860 945.1, dated Oct. 24, 2019, 10 pages.

\* cited by examiner

US 10,972,884 B2

RULES-BASED RIDE SECURITY

CLAIM OF PRIORITY

This application claims priority under 35 USC § 119(e) to U.S. Patent Application Ser. No. 62/248,687, filed on Oct. 30, 2015, the entire contents of which are hereby incorporated by reference.

BACKGROUND

On-demand mobility is a trend in transportation services today. On-demand mobility relates to moving people, goods, or services with the assistance of a computer, such as an application operable on a mobile computing device, that allows for ease of scheduling and payment. On-demand mobility services can bring convenience to user's lives. In some cases, the security and privacy of users can be diminished with this convenience.

SUMMARY

In a general aspect, a method includes receiving, through the user interface of a user device of a user, a request for a ride from the user; assigning a driver to provide the ride for the user; according to one or more application rules associated with the request for the ride, providing the driver with access to information uniquely identifying the user or a rider.

Embodiments can include one or more of the following features.

Providing the driver with access to the information includes providing the driver with access based on a location of the driver, in which the application rules define the location at which the driver is to be provided with access.

The method includes providing the driver with access to the information at a pick-up location for the ride.

Providing the driver with access to the information includes providing the driver with access for a limited period of time, the limited period of time being specified by one or more of the application rules.

The method includes causing destruction of the information according to one or more of the application rules.

The method includes causing destruction of the information after the driver has accessed the information.

The method includes receiving, from a mobile device operated by the driver, a current fingerprint of the user; and in which providing the driver with access to the information includes providing the driver with information indicative of results of a comparison between the current fingerprint of the user or rider and a stored fingerprint of the user or rider.

The method includes providing the driver with access to one or more instructions associated with the ride according to one or more of the application rules.

The instructions include one or more of audio instructions, video instructions, image instructions, and text instructions.

In an aspect, a method includes receiving, through the user interface of a user device of a user, a request for a ride from the user; assigning a driver to provide the ride for the user; according to one or more application rules associated with the request for the ride, providing the user with access to information uniquely identifying the driver.

Embodiments can include one or more of the following features.

The information uniquely identifying the driver includes a visual code.

The visual code includes a pattern of colors.

The method includes providing the visual code to a mobile device associated with the driver.

The visual code is randomly generated based on the one or more application rules and in which the randomly generated visual code is synchronized between the mobile device associated with the driver and a mobile device associated with the user.

The visual code provided to the mobile device is configured to be displayed with one or more lights mounted on a vehicle operated by the driver.

The method includes receiving, from a mobile device operated by the user, a current fingerprint of the driver; and in which providing the driver with access to the information includes providing the driver with information indicative of results of a comparison between the current fingerprint of the driver and a stored fingerprint of the driver.

In an aspect, a method includes during transportation of a rider by a driver in a ride arranged by a computer-implemented driver assignment platform, implementing one or more rules to enable an image of the rider to be transmitted to one or more of an operator of the computer-implemented driver assignment platform and a supervisor of the rider.

Embodiments can include one or more of the following features.

Enabling an image of the rider to be transmitted includes streaming a live video of the rider.

The method includes adjusting the bandwidth of the streaming video by upscaling or downscaling of video during live video streaming.

Enabling an image of the rider to be transmitted includes capturing pictures or bursts of pictures of the rider and the car and transmitting the pictures or the bursts of pictures.

The method includes enabling transmission of a map depicting a predicted route of the ride and a current approximate location of the rider on the map.

The method includes preventing one or more functions of a device of the driver from being operational during the ride.

The method includes enabling the rider to generate a panic alert, using a rider device, responsive to a distress situation occurring during the ride.

In an aspect, a method includes during transportation of a user by a driver in a ride arranged by a computer-implemented driver assignment platform, receiving information indicative of a location of the ride; implementing one or more application rules to compare the received information indicative of a location of the ride with information indicative of an allowed boundary of the ride; and generating an alert when the location of the ride deviates from the allowed boundary of the ride.

Embodiments can include one or more of the following features.

The method includes establishing a geo-fence for the ride defining an area around the expected path of the ride, the geo-fence being based on the one or more application rules associated with the rider; and generating the alarm when the ride leaves the area defined by the geo-fence.

DETAILED DESCRIPTION

In on-demand transportation services, in which a service provider (e.g., a driver) takes a service receiver (e.g., a rider) from one point to another in a private vehicle, the security of users and riders are important. The approaches described here enable users and drivers to securely identify each other to ensure that a requested ride is provided by the intended driver to the intended driver. The approaches described here also enable monitoring of the status or behavior of the driver and/or the rider during the ride, e.g., via streaming video, images, or audio. The approaches described here also enable monitoring of the location of the driver's vehicle during the ride.

Figure 1:
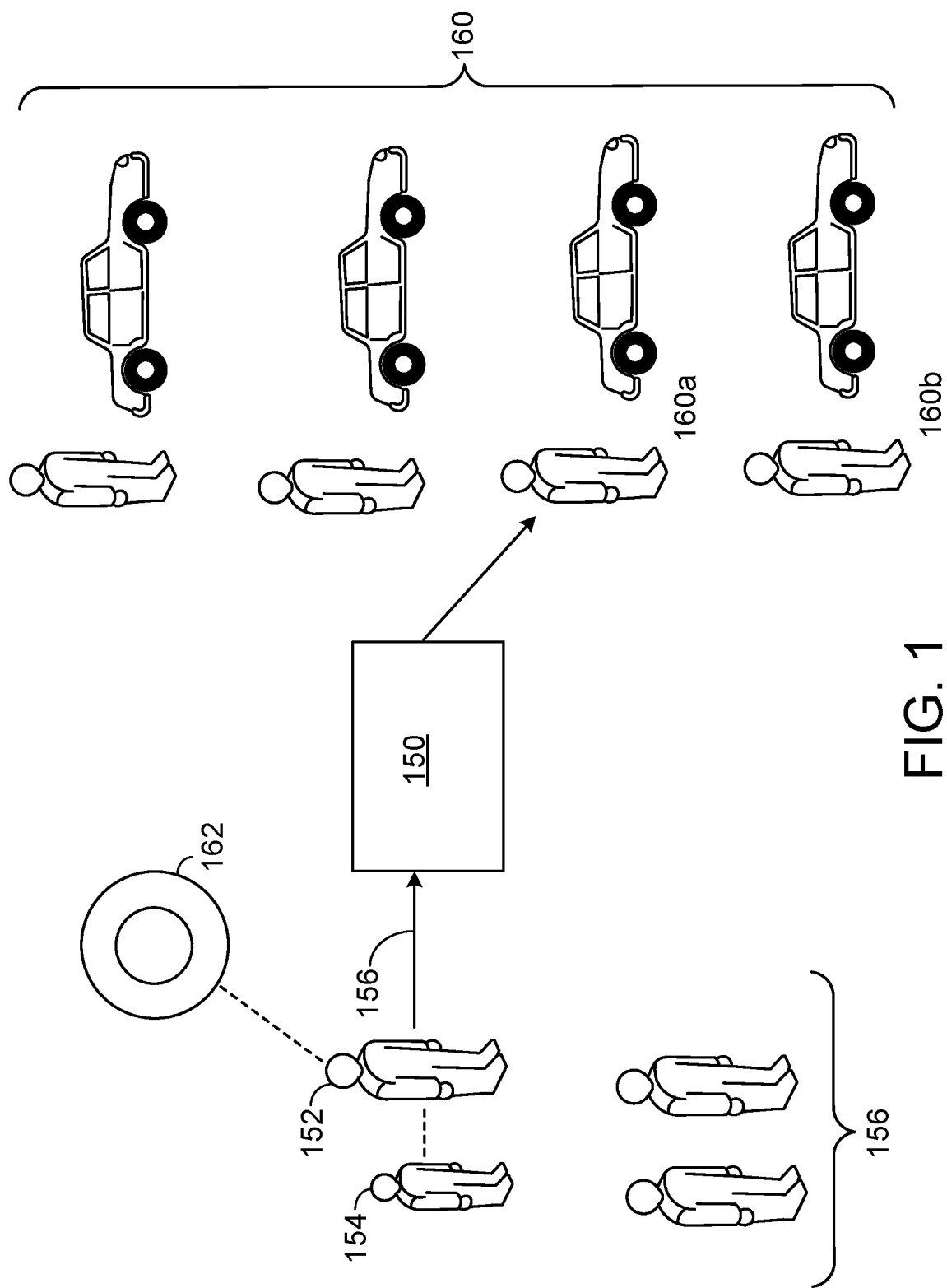
FIG. 1 is a diagram of an on-demand and scheduling service system.

Referring to FIG. 1, an on-demand and scheduling service system 150 receives a request 156 for a ride from a user 152. In some examples, the user 152 requests the ride for himself; in some examples, the user 152 requests the ride on behalf of a rider 154. The request for a ride can include schedule information, such as the date and time of the ride; geographic information, such as a start location, a waypoint, and an end location; special requests, such as a request for a vehicle that can accommodate luggage; and/or other types of information.

Multiple drivers 160 are enrolled with the on-demand and scheduling service system 150. Responsive to receiving the user's request 156 for a ride, the on-demand and scheduling service system 150 selects a particular driver 160a from among the multiple drivers 160 and assigns that driver 160a to provide the ride for the user 152 or the rider 154. The on-demand and scheduling service system 150 can select the particular driver 160a from among the multiple drivers 160 based on an indication of the trust that the user 152 has for each of one or more of the drivers 160. For instance, the particular driver 160a selected by the on-demand and scheduling service system 150 for the user 152 can be the driver who is the most trusted by the user 152, based on one or more metrics of trust, such as based on a circle of trust for the user and/or based on a trust barometer value for the driver. In some examples, the on-demand and scheduling service system 150 can determine an indication of the trust that the user 152 has for each of the one or more drivers 160 upon receipt of the user's request 156 for a ride. In some examples, the indication of trust can be pre-determined and stored in a data storage associated with the on-demand and scheduling service system. Further description of trust-based selection of drivers can be found in U.S. Pat. No. 10,325,228, issued on Jun. 18, 2019, the entire contents of which are incorporated here by reference.

One or more measures can be implemented by the on-demand and scheduling service system 150 to maintain the safety and security of the rider 154 during the ride. In some examples, the driver 160 can be subject to one or more background checks 170. In some examples, the system 150 can enable identity verification 172 to ensure that the driver 160 picks up the intended rider 154 and that the rider 154 accepts a ride with the intended driver 160. For instance, the driver 160 can be provided with information to verify the identity of the user 152 or the rider 154 at pick-up, or the user 152 can be provided with information to verify the identity of the driver 160 at pick-up. The system 150 can facilitate the transmission of images or video of the rider 154 in real time 174 to the user 152 or to another third party during the ride to allow the user or third party to monitor the status of the rider 154. The system 150 can monitor the ride 176, such as the location of the driver's vehicle, and transmit an alert to the user 152 or to another third party if an unexpected action is taken, such as if the driver 160 deviates from an expected route for the ride.

In some examples, to maintain the safety and security of riders using the on-demand and scheduling service system 150, the drivers 160 can be verified and background checked, e.g., upon registration with the system, periodically, or at random intervals. For instance, during a driver's registration with the on-demand and scheduling service system 150, each driver completes a screening process. One or more activities can be performed in this screening process to verify the driver, such as collection and verification of the driver's personal information and documentation, interviews, trainings, mentoring by a coach, background checks, Department of Motor Vehicles (DMV) checks, reference checks, or other activities. Particulars of the driver's license, vehicle insurance, motor vehicle records, social security number, federal, county, or multi-state criminal records can also be verified.

In some examples, the user 152 can be provided with information to verify the identity of the driver, for instance, to verify that the driver 160 who has arrived to pick up the rider 154 is the same driver that was assigned to the user's requested ride 156. The information can include personal information, such as a name, photograph, demographic information, or other personal information. The information can include information about the driver's vehicle, such a description of the vehicle (e.g., a make and model of the vehicle), a photograph of the vehicle, the vehicle's license plate, or other information about the vehicle.

In some examples, fingerprints of a driver can be taken, such as at the time of registration. The fingerprints can be taken through the driver's computing device or at a central facility, such as a registration facility, and stored in a database of the on-demand and scheduling service system 150. When the driver 160 arrives to pick up the rider 154, the user 152 can obtain the driver's fingerprints, e.g., via the user's mobile device, and the system 150 can compare the obtained fingerprints with the stored fingerprints of the driver who is scheduled for the ride. If the fingerprints match, the driver 160 is verified as the correct driver.

In some examples, the on-demand and scheduling service system 150 can provide the driver 160 and the user 152 with a code 178 that uniquely identifies the driver 160. The driver 160 and the user 152 can compare their codes at pick-up to ensure that the driver 160 is picking up the correct rider 154 and that the rider 154 is accepting a ride with the correct driver 160. The code 178 can be a visual code, such as a pattern of colors. The code can be a static code or a dynamic code, e.g., a pattern of changing colors. In some examples, the code can be displayed on the user interface of a mobile device operated by each of the driver 160 and the user 152. In some examples, the driver's vehicle can be equipped with one or more lights that light up or flash to display the code on the driver's vehicle, thus helping the user 152 to identify the driver's vehicle even at a crowded pick-up location.

In some examples, the driver 160, the rider 154, or both can be monitored during the ride by the on-demand and scheduling service system 150, and information obtained by the monitoring can be provided to the user 152 or to a third party, such as a system administrator of the system 150. The monitoring can include capturing video and/or still images of the driver 160, the rider 154, or both, continuously throughout the ride or at regular or random intervals, and providing the captured video and/or images to the user 152 or third party. The monitoring can include monitoring driver behavior, such as speed, acceleration, use of mobile devices, or other behavior. The monitoring can include monitoring the route of the driver's vehicle during the ride. In some examples, if the driver's vehicle deviates from an expected route, an alert can be provided to the user 152 or to a third party.

Figure 2:
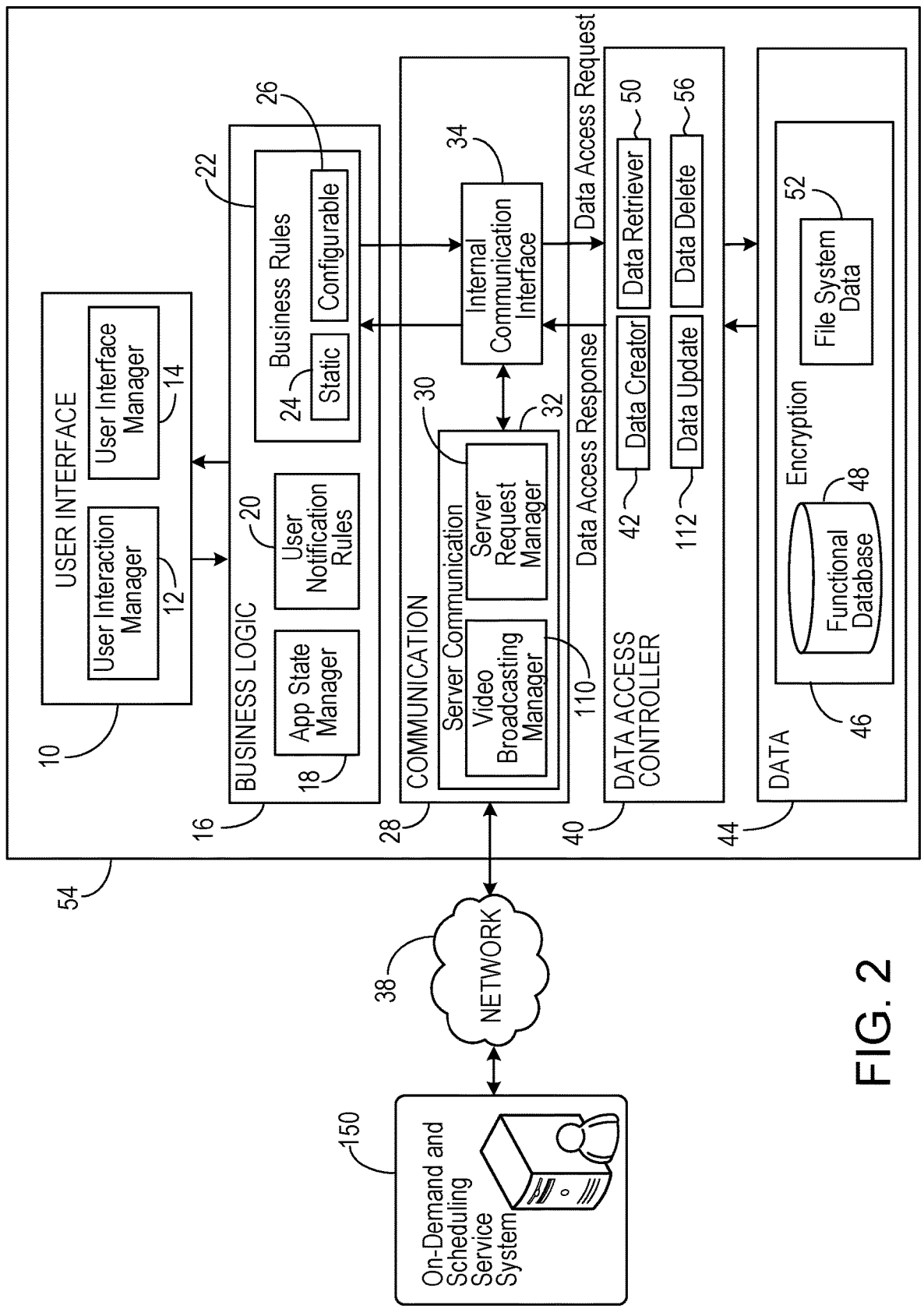
FIG. 2 is a diagram of an on-demand scheduling service system.

FIG. 2 shows a diagram of an example of the on-demand and scheduling service system 150. The on-demand and scheduling service system 150 includes a client device 54. The client device 54 can be one or more of a user's device, driver's device, rider's device, third-party user's device, and so forth. In some examples, the user is the rider. In some examples, the user is the third-party user, such as a requestor of the ride that is neither the rider nor the driver. The on-demand and scheduling service system 150 includes an on-demand and scheduling service system server 35. The server 35 can be a remote computing device for storing data, performing calculations, managing rulesets associated with each user, rider, and driver of the system 150, and other similar functions. Determinations of the system, such as those made by the application logic 16, can be performed either client-side, server-side, or both. Each of the server 35 and the client device 54 communicate over a wireless network 38, such as a cellular network, the Internet, and so forth.

Each of the server 35 and the client device 54 of the system 150 can include an application logic device 16, 17, a communication module 28, 29, a data access controller 40, 41, and a data handling module 44, 45. For example, when the client device 54 receives input though a user interface 10 of the client device 54, the communication module 28 can send the instructions for processing server-side by the application logic 17 of the server 35, or the instructions can be parsed and processed by the application logic 16 of the client device 54.

Each of the server 35 and the client device 54 of the system 150 include application logic devices 16, 17. The application logic devices 16, 17 include data processors for managing instructions of the application, determining the application state, processing inputs to the application from the user, and fetching or obtaining application rules for determining functionality of the application of the system 150. In some examples, the application of the system 150 is a program running on the client device 54 and/or the server 35 for performing the functions described herein.

The application logic module 16, 17 includes an app state manager 18, 19, a user notification rules module 20, 21, and the application rules module 22, 23. The app state manager 18, 19 monitors and controls the state of the application, which can determine content of a response sent by the application in response to input by the user or data received by the application. The user notification rules module 20, 21 determines when notifications, such as alerts, SMS messages, emails, alarms, push notifications, etc. are sent to the user. The application rules module determines which rules are applied during operation of the application as described in further detail below. The application rules engine includes rulesets that are both static, such as static rules 24, 25, and configurable by a user, such as configurable rules 26, 27.

The application rules engine communicates with the internal communication interface 36, 37. The internal communication interface 36, 37 manages requests and responses from various modules of the server 35 or client device 54 of the system 150. For example, when data is requested from the functional database 48, 49, the internal communication interface 37, 38 can send a request for the data, receive the data in response, and route the data to the appropriate requesting module.

The communications module 28, 29 includes either a client communication module 31 or a sever communication module 30 for the server 35 and client device 54, respectively. The client communication module 31 includes a client request manager 33 for handling (e.g., queueing, parsing, etc.) requests from the client device 54. The server communication module 30 includes a server request manager 32 for handling (e.g., queueing, parsing, etc.) requests from the server 35.

Video broadcasting managers 110, 111 use the data retriever components 50, 51 of the data access controller 40, 41 to broadcast the live video of rider according to application rules 22, 23. Data creator components 42, 43 are used to store this video data in the functional database 48 of the on-demand and scheduling service system 150. Data update modules 112, 113 and data delete modules 55, 56, can be used for managing, updating, deleting, and maintaining data of the data module 44, 45, such as according to application rules 22, 23.

The data module 44, 45 stores and organizes data of the server 35 and client device 54 as required by the application rules 22, 23. For example, data for users can be stored in the function database 48, 49, such as demographic data of users, riders, etc. User preferences can be stored, such as preferred routes, no-go zones, geo-fences, a trusted driver list for that user, an image of the user, saved pickup instructions, and so forth. The data module 44, 45 also handles file system data 52, 53 required for running the application, such as system files and the like.

The client device 54 includes a user interface 10. The user interface 10 can be a touch screen, display, monitor, and so forth. The user can input commands via the user interface and otherwise interact with the application of the system 150 using the user interface 10. The user interaction manager 12 and user interface manager 14 are described in greater detail below.

A user (e.g., a customer or requestor) as described here refers to an individual who makes a service request to the on-demand and scheduling service system 150. The service provider can be an individual or entity that can provide the service requested by user. The service receiver can be an individual to whom the requested services are provided. A user or customer, using a customer device, can request an on-demand or scheduling service which can be a transport service, a telegram service, food delivery service, or a messenger service. The on-demand and scheduling service system 150 can communicate with the service providers using the provider devices and arrange for them to provide the requested service.

User inputs making up the request for a ride are converted into data by a client device 54 and sent to the on-demand and scheduling service system 150. In some examples, the client device 54 includes a mobile computing device, such as a smart phone, tablet, smart watch, and so forth. In some examples, a user's device, a driver's device, a rider's device, etc. can be a client device 54. In some examples a portion of the data that is sent to the system is relies on user input, and other information might be fetched from the client device 54 that the user is using. In some examples, more information might be fetched from the functional database 48. The request can be sent out of the device through a network 38 interface of the client-end computing device 54.

The inputs given by the user in the client device 54 can be received by a user interaction manager 12 that is a component of a user interface 10. In some examples, the user interaction manager 12 forwards the user's request to an internal communication interface 34 for sending it to the on-demand and scheduling service system 150 according to application rules 22 (e.g., data processing rule), discussed below. The application rules 22 can either be static 24 or configurable 26. Along with this request there can be data related to the request. For example, in addition to the data sent by the client device 54 there is some data that are already present in the on-demand and scheduling service system 150. There are also data present in a functional database 48 which can include the trust-related data of a user for one or more drivers. Some data can be directly collected from the driver when the driver registers with the service, and some data can be updated after registration. For instance, data can be updated by the driver or based on actions taken or reviews received by the driver. The trust-related data is stored in the database of the on-demand and scheduling service system 150. After receiving the request sent by the client device 54, the on-demand and scheduling service system 150 verifies one or more components of the request, such as for whom the ride request is made, pick-up or drop-off locations, time of pick-up (such as whether the ride is requested for now or scheduled for a later time), that only one ride is requested for a rider at one time, or other components of the request. In one example, the on demand and scheduling service system 150 can forward the user's request to the driver who is most trusted by the user and/or to one or more drivers having trust of the user for acceptance or the request. Forwarding can be done using the data that was sent to the on-demand and scheduling service system 150 by the client device 54 of the user, and the data that is already present in the functional database 48. The on-demand and scheduling service system 150 can notify the user that a response is requested from the user's trusted driver to accept the user's ride request.

In some examples, the on-demand and scheduling service system 150 can maintain photographs of riders, users, drivers, and/or other people. For instance, the user can take a photograph of a rider (e.g., a child) using the camera component of the user's client device 54 or can use a previously taken photograph. The picture can be sent to the on-demand and scheduling service system 150 through the network 38 interface of the client device 54 of the user, e.g., upon registration of the user or rider or upon the user requesting the ride. A data retriever 50 component of the data can access the controller 40 from the on-demand and scheduling service system 150 through the server request manager 32. The user interface manager 14 of the client device 54 of the driver can be used to display the rider's picture to the driver according to application rules 22. In some examples, video instructions or permissions (discussed below) can be recorded, e.g., using the camera hardware component of the user's device. The on-demand and scheduling service system 150 can send these instructions to the client device 54 of the driver through the network 38 interface of the device according to the application rules 22.

Capabilities of the on-demand and scheduling service system 150 can be accessible to the user, the driver, or both through an interface of an application executed on a mobile device. Through the interface, the user can provide instructions, confirm the identity of the driver, monitor the progress of a ride, or take other actions. Through the interface, the driver can view the user's instructions, confirm the identity of the user or rider, or take other actions.

Figure 3:
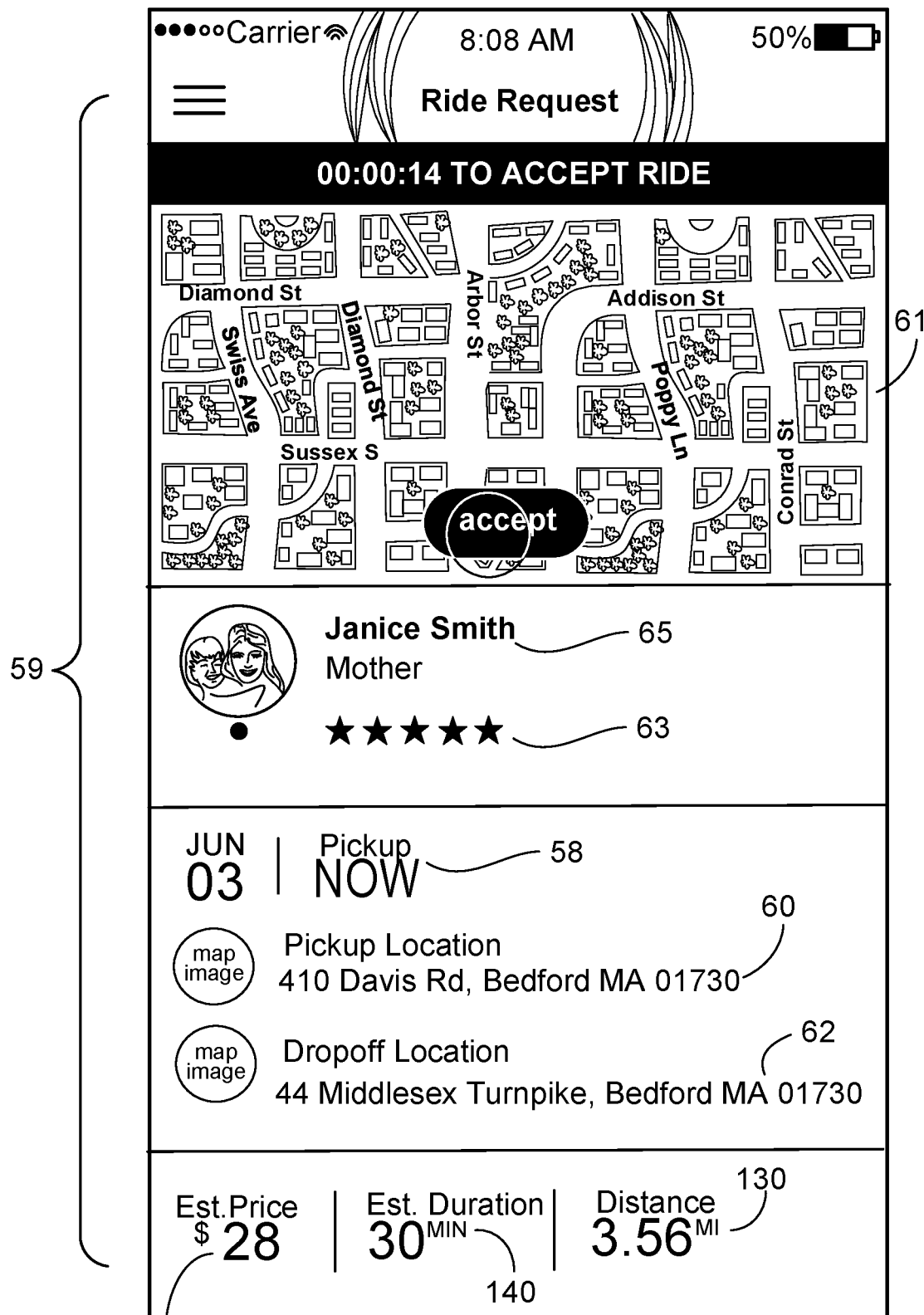
FIGS. 3-21 are diagrams of user interfaces.
Figure 4:
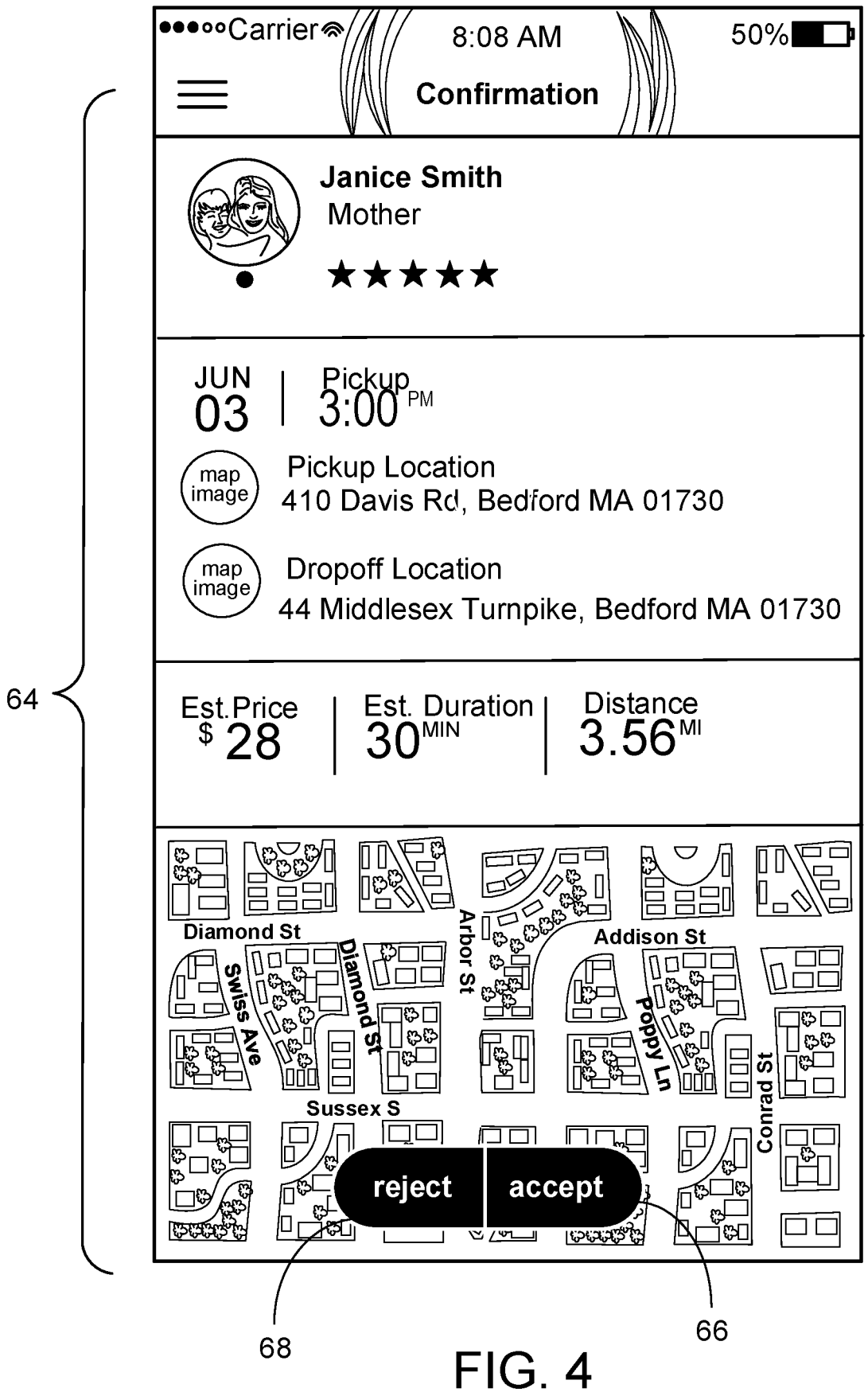

In some examples, information about the user or rider can be provided to the driver prior to the beginning of the ride, e.g., when the driver is selected to provide a ride to the user. Referring to FIG. 3, a driver who has been selected to provide a requested ride for a user can view information about the ride and instructions from the user via a user interface 59. For instance, when a user makes a request for a ride, the user can provide information such as pick-up location 60, drop off location 62, pick-up time 58 and date, or other information. This information provided by the user can be displayed in the driver's user interface 59. The distance 130, duration 140 of the trip, estimated cost 150, and other such information about the trip can be estimated by the system and displayed in the driver's user interface 59. In some examples, a map 61 of one or more of the route, destination, the current location of the user or rider, or the current location of the driver can be provided in the user interface 59. A name 65 of the user and/or rider and the user's relationship to the rider can be provided. In some examples, other information about the user or the rider can be provided, such as an image of the user or rider, a rating 63 of the user or rider (indicating, for example, a reliability of the user, a behavior of the rider, etc.), or other information about the user or the rider. If the rider is a child or other person who may need supervision, the user can assign and provide information relating to a supervisor who is expected to or who has permission to hand over the rider to the driver at the time of pick-up. If the information about the requested ride is acceptable to the driver, the driver can accept the ride via the user interface 59. Referring to FIG. 4, once accepted, a confirmation interface 64 showing the details of the ride is displayed and the driver is given another opportunity to accept or reject the requested ride via controls 66, 68.

Figure 5:
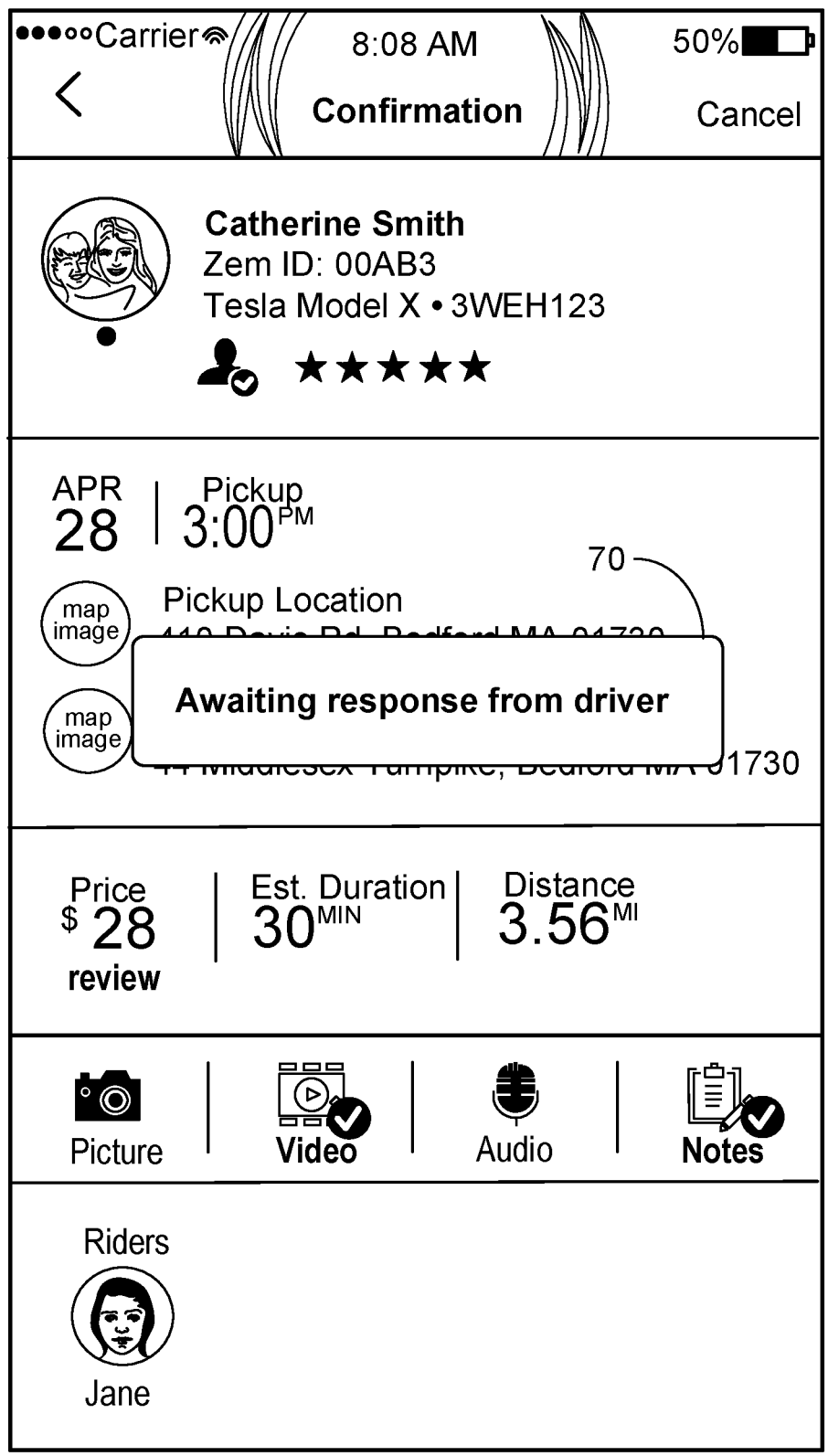
Figure 6:
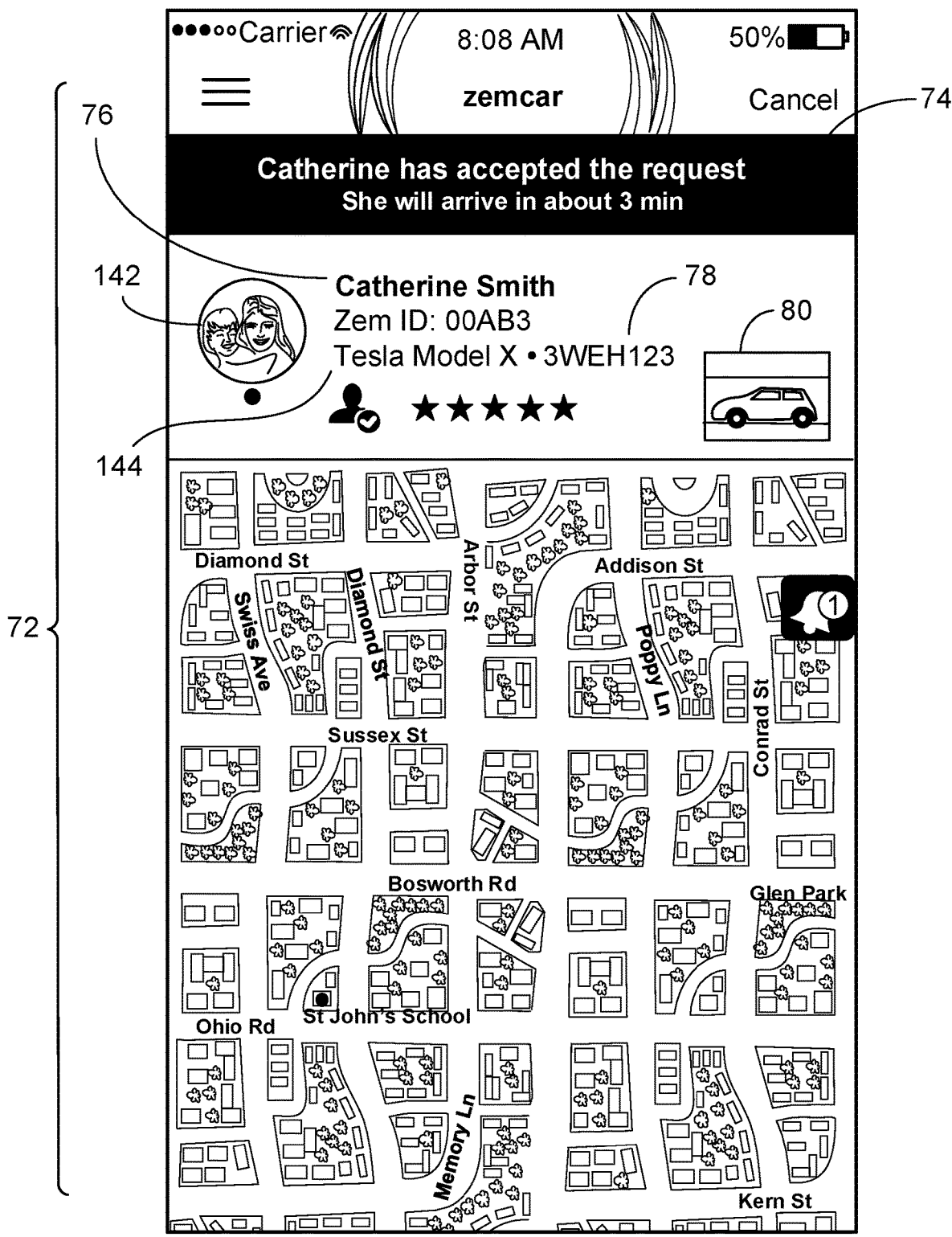

In some examples, information about the driver assigned to provide a ride for a user can be provided to the user prior to the beginning of the ride. Referring to FIG. 5, while the user waits for the driver to accept and confirm the ride, the user views a user interface that includes information about the ride and an indicator 70 that a response from the driver is needed. Referring to FIG. 6, when the driver accepts and confirms the ride, the user receives a notification interface 72 including information about the assigned driver, such as the driver's name 76, profile picture 142, driver identification number, driver rating or feedback or reviews, and/or other information. The user is also shown information about the driver's vehicle, such as a description of the vehicle 144 (e.g., make and model of the car, car color, or other description), a photograph of the vehicle 80, the vehicle's license plate number 78, and/or other information. The user can be provided with an estimate 74 of when the driver is expected to arrive at the pick-up location. In some examples, the real time location of the driver can be tracked on a map so that the user can monitor the driver's progress.

Figure 7:
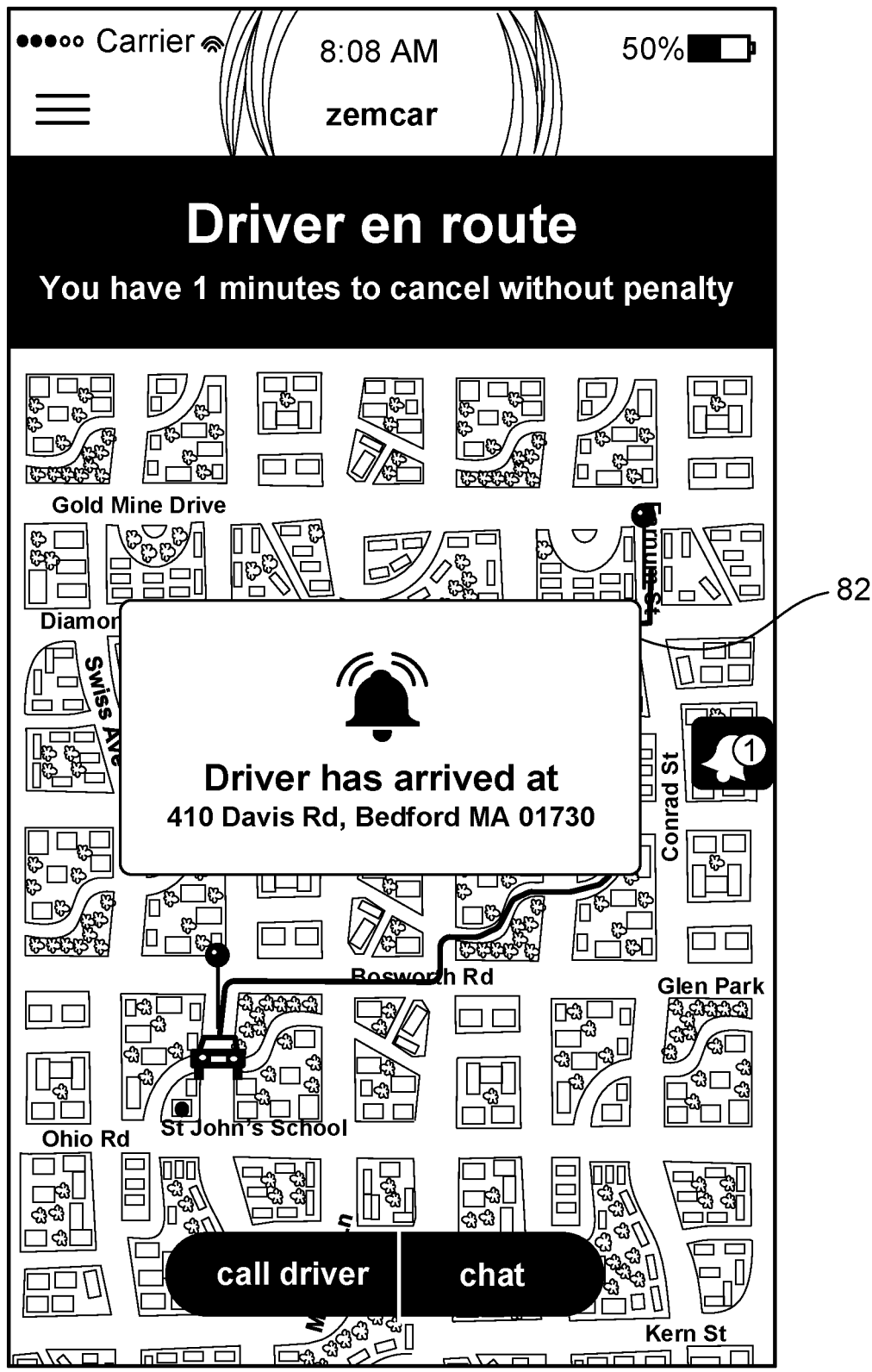

Referring to FIG. 7, once the driver has started driving toward the pick-up location, the user is shown a status interface indicating that the driver is en route. In some examples, a penalty can be assessed if the user cancels the ride request after a certain point, such as after the driver has started driving, after the driver has been driving for a certain amount of time, after the driver has arrived at the pick-up location, or at another point. A notification 82 is displayed when the driver arrives at the pick-up location. While the driver is en route, the user is given the option to call or chat with the driver.

In some examples, the driver can be provided with information and instructions relevant to the requested ride. For instance, the information and instructions can help the driver to identify the user and/or the rider. The information and instructions can be provided to the driver as images, video, audio, or text, or in another form. In some examples, the information and instructions are provided to the driver according to one or more rules, e.g., default rules or rules established by the user. For instance, the rules can govern when the driver can have access to the information and instructions, how many times the driver can access the information and instructions, what happens to the information and instructions after having been accessed by the driver, and so forth.

In some examples, the user can be provided with information to verify the identity of the driver, e.g., to ensure that the rider accepts a ride from the driver who has been assigned for that rider. The information can help the user to identify the driver and/or the driver's vehicle. The information can include information about the assigned driver, such as the driver's name or picture and/or other information. The information can include information about the driver's vehicle, such as a description of the vehicle (e.g., make and model of the car, car color, or other description), a photograph of the vehicle, the vehicle's license plate number, and/or other information. The information can include fingerprints of the driver. The information can include a visual identifier, such as a visual code to be displayed on the driver's mobile device or vehicle that can be matched to a visual code displayed on the user's mobile device. In some examples, the information to verify the identity of the driver can be provided according to one or more rules, e.g., default rules or rules established by the user. For instance, a user who is less concerned about security can set rules such that identity verification of the driver is performed only by confirming the license plate number of the driver's car. A user who is more concerned about security can set rules such that identity verification of the driver is performed by a combination of license plate verification, fingerprint verification, and verification of a visual code displayed on the driver's vehicle.

Figure 8:
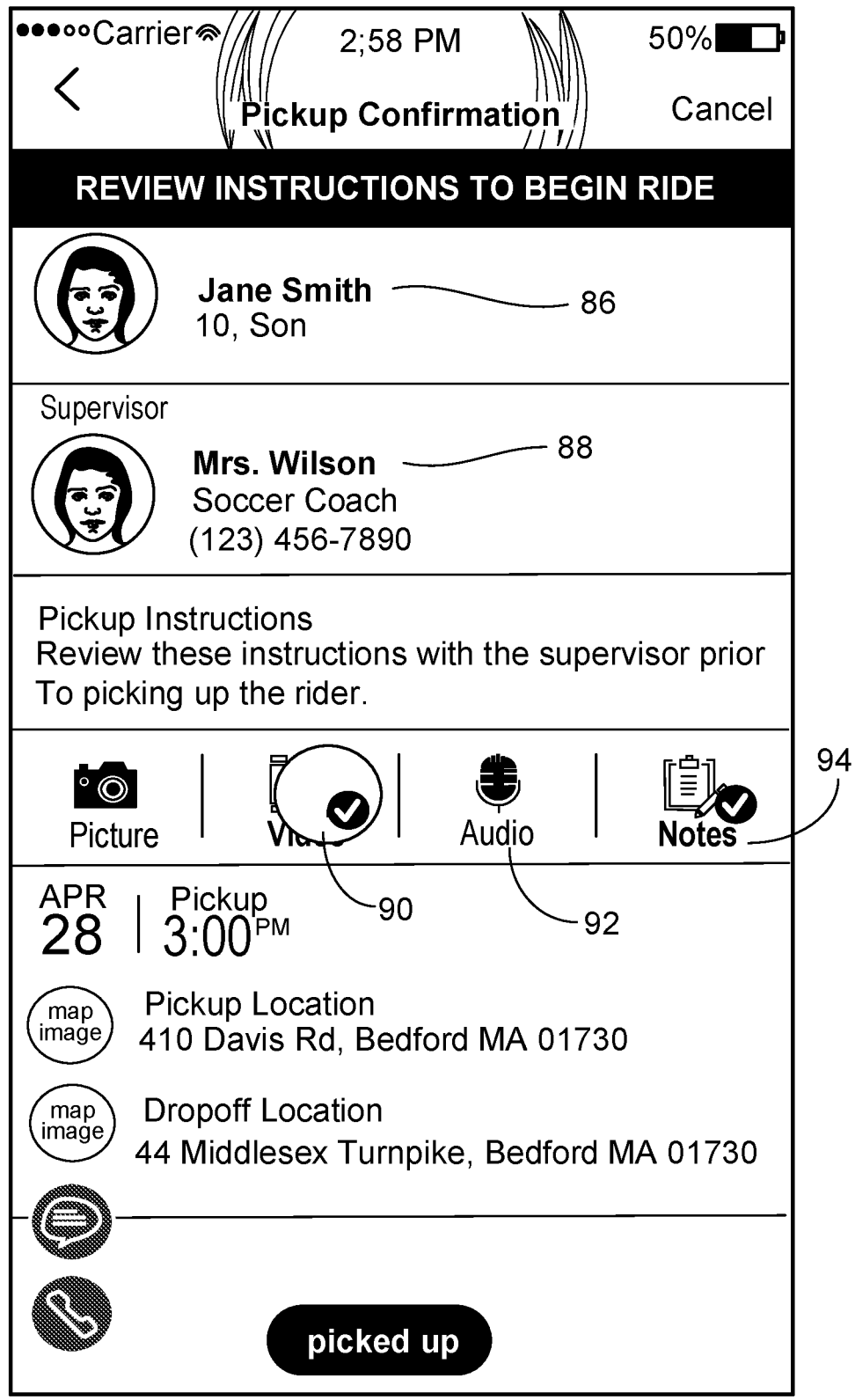

Referring to FIG. 8, a pickup interface 84 provides the driver with information and instructions relevant to the requested ride. When requesting the ride, the user can set up instructions or permissions, e.g., to help ensure that the driver picks up the proper rider or that a child rider is released into the care of an allowed adult at the pick-up location, to provide any special instructions related to the care of the rider, or other instructions or permissions. Identity verification can be done at the time of pickup. The instructions or permissions can include audio, video, text and/or pictures.

In some examples, the pickup interface 84 for a driver can include information 86 identifying the rider and information 88 identifying a supervisor of the rider, such as the user who requested the ride, a person supervising the rider at the pick-up site, a person who will receive the rider at the drop-off site, or another supervisor. The information 86, 88 can include the name of the rider and/or supervisor, phone number of the supervisor, photographs of the rider and/or supervisor, information regarding the relationship between the rider and the supervisor, and so forth. In some examples, the driver can verify the identity of the rider by scanning the rider's fingerprints, as discussed below. Verification of the rider's identity helps ensure that the driver is picking up the rider for whom the ride is intended, and that the rider remains in the care of an appropriate person. For instance, a photograph of the rider can help the driver to recognize the rider, e.g., if the pick-up location is crowded, and also serves as verification of the identity of the rider and helps to ensure that the driver picks up the proper rider.

The interface 84 can include controls 90, 92, 94 for viewing video, audio, or text instructions, respectively, provided by the user with the request for the ride. Pictures of instructions can also be provided and accessed by a control. Example instructions can include requests for photographs, videos, audio, text messages, or other types of information to be sent to the user or another third party upon pick-up, during the ride, and/or at drop-off.

In some examples, the instructions or permissions for a ride can be date- and time-stamped such that a driver knows that he is viewing up-to-date instructions or permissions. In some examples, the instructions or permissions have access limitations, e.g., the instructions or permissions can be accessed by the driver only at certain times, such as once the driver accepts the ride, once the driver arrives at the pick-up location, or at other times. In some examples, the instructions or permissions can self-destruct, e.g., after access by the driver, after a certain amount of time, or at a certain point in the ride (e.g., after pick-up of the rider or after drop-off of the rider). The time for destruction of the pictures, video, or other information can be set by default or can be specified by the user. Self-destruction helps to ensure that the instructions or permissions are not shared or misused. In addition, self-destruction of instructions helps to ensure that instructions are not erroneously used for a subsequent ride, e.g., a ride provided by the driver to another user or to the same user. In an example, the driver can be shown a photograph of the rider only once the driver arrives at the pick-up location. The rider's photograph can self-destruct once the driver indicates that the rider has been picked up. These access permissions and self-destruction provide the driver with enough time to find the rider at the pick-up location but do not allow the driver any time to otherwise handle the photograph.

Figure 9:
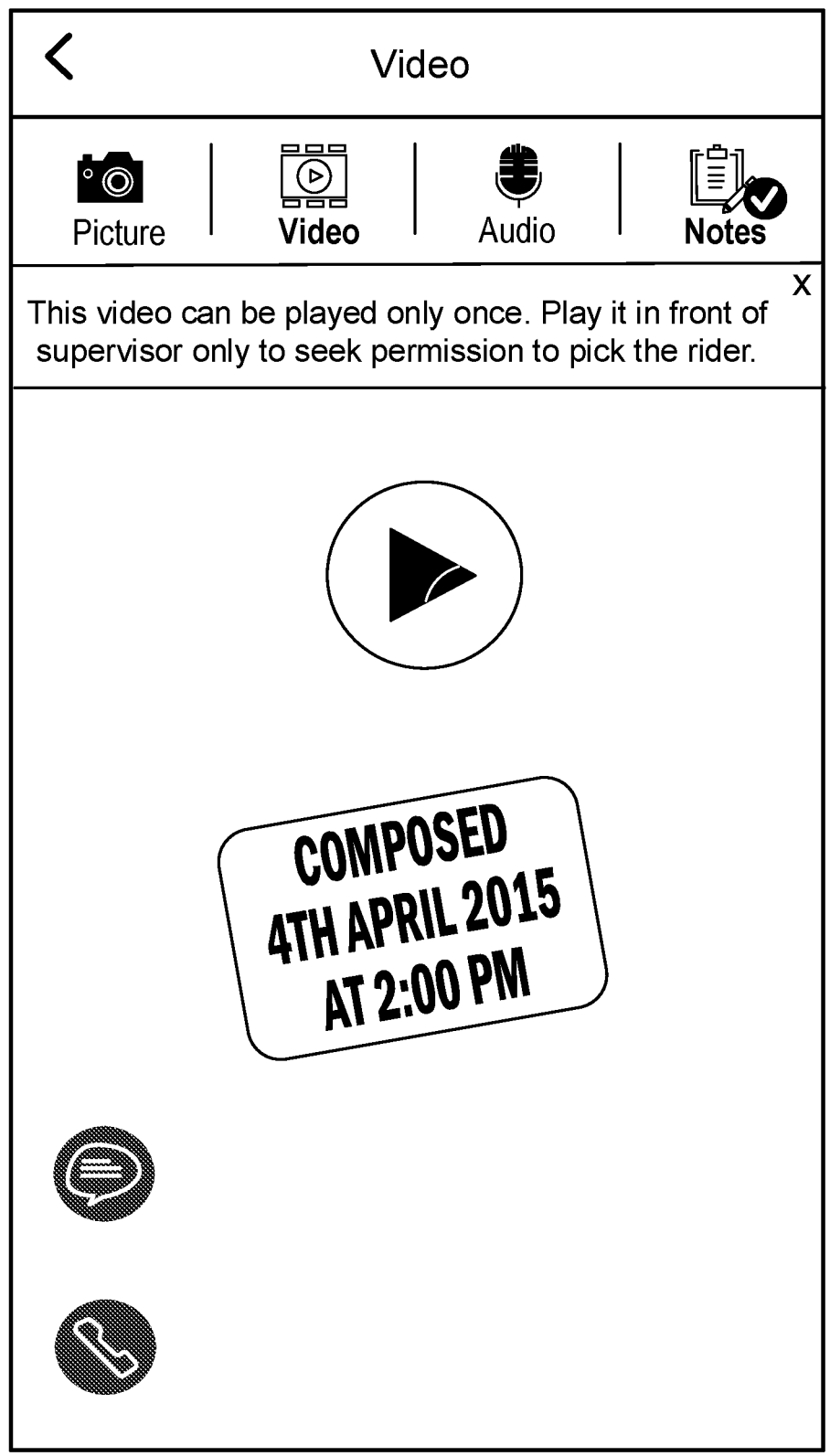
Figure 10:
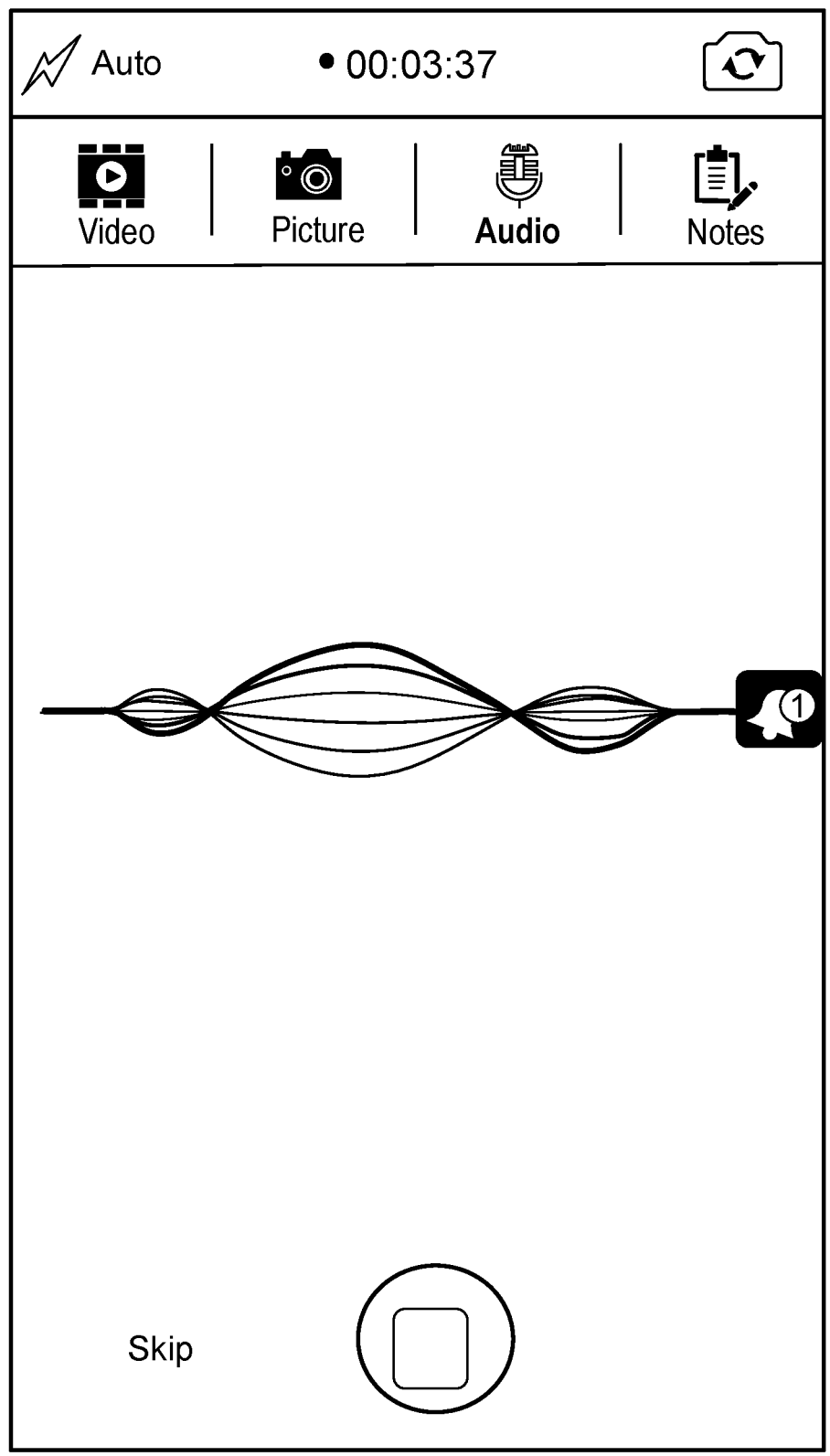
Figure 11:
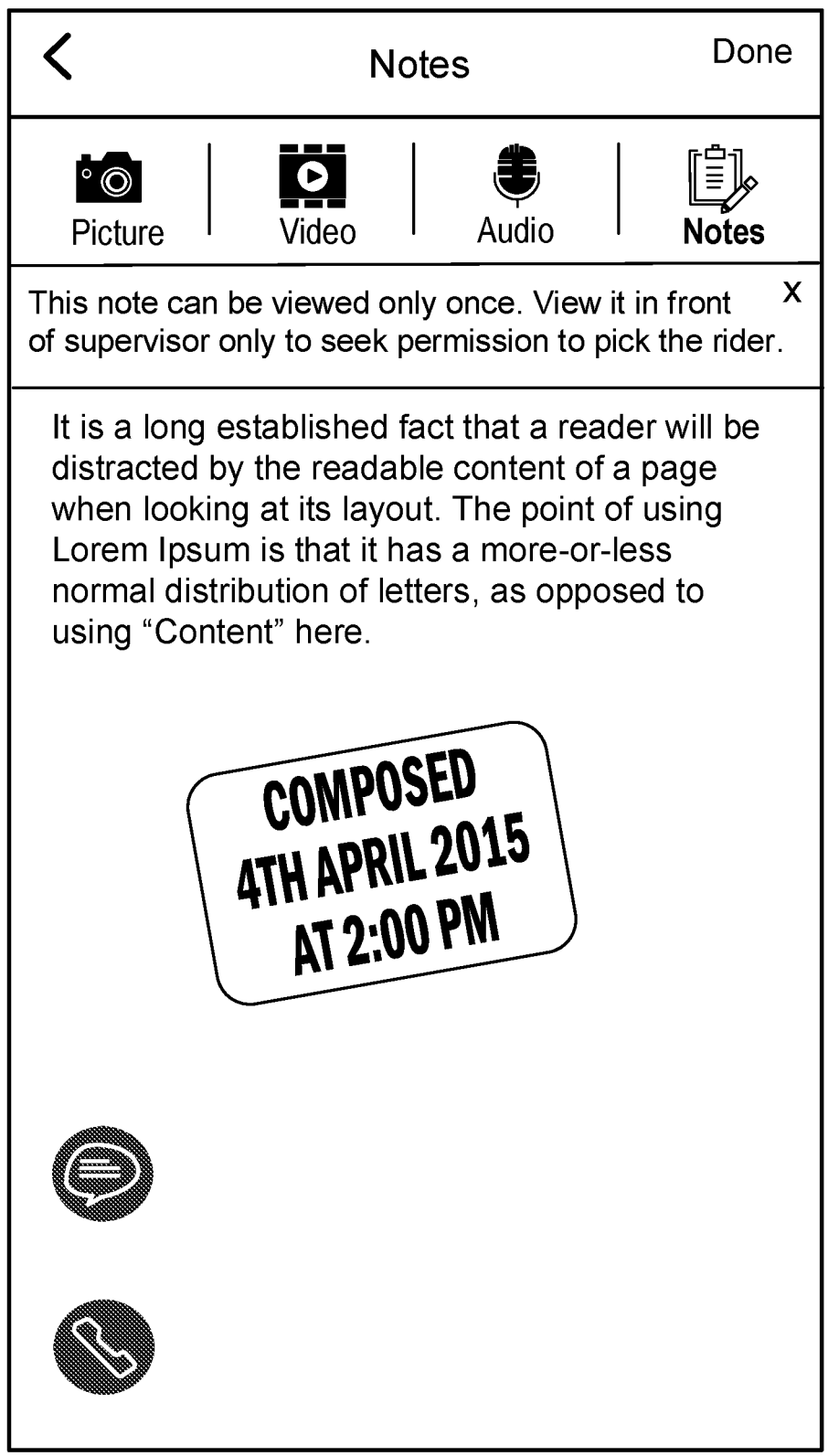

FIGS. 9-11 show example instruction interfaces for the driver to access video, audio, and text instructions, respectively. In some examples, a control for starting the video or audio instructions can be provided. In some examples, the video or audio instructions can start automatically when accessed by the driver. The instructions can be configured to play or be seen a single time, or during a specific time period, such as when the driver accepts the ride, immediately after the driver has arrived at the pickup location, or at another time. For example, the instruction might be active for only one minute after the driver arrives such that a third party cannot see the instructions or so that a supervisor of the rider can be sure that the driver is properly verified. The instructions can include a date and time of composition.

Fingerprint verification can be performed by scanning one or more fingerprints scanner component of a device, such as the user's device or the driver's device. In some examples, the user can scan the driver's fingerprints to verify the driver's identity; in some examples, the driver can scan the rider's fingerprints to verify the rider's identity or can scan the fingerprints of a person receiving the rider at the drop-off location to verify that the receiving person is authorized to have custody of the rider.

The scanned fingerprints can be matched with one or more original fingerprints of the driver stored in a database of the on-demand and scheduling service system 150, such as the functional database 48. For instance, when the driver's fingerprints are scanned through user's device at pick-up, the server request manager 32 can retrieve the driver's original fingerprints from the functional database 48 using the data retriever 50 component of the data access controller 40. If the scanned fingerprints match the stored fingerprints, the user can allow the driver to pick up the rider.

Figure 12:
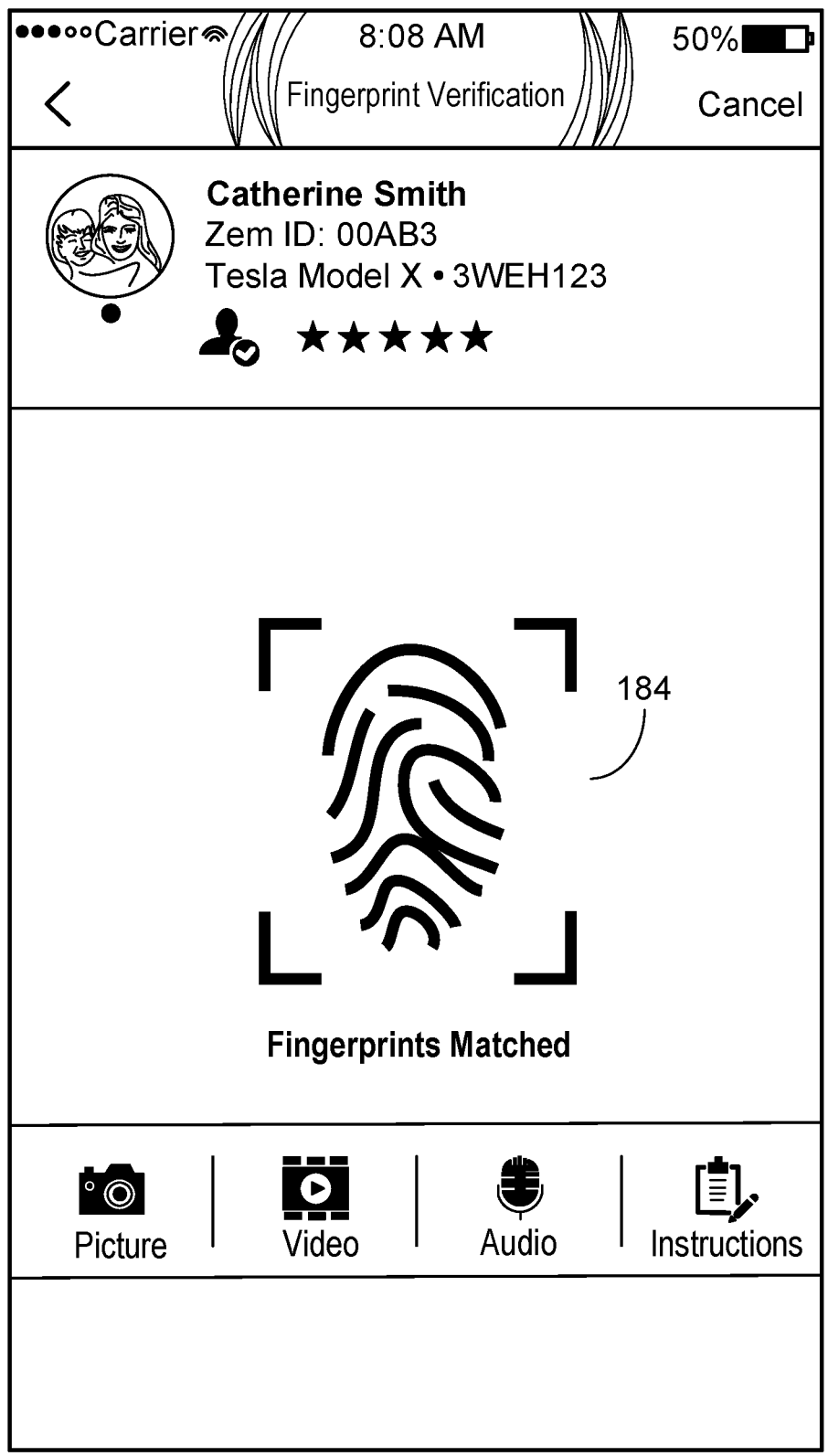

Referring to FIG. 12, an example fingerprint interface 184 on a user's device displays an indication that the driver's scanned fingerprint has matched the stored fingerprint for the driver. With fingerprint verification, the user can feel confident that the driver who has arrived at the pick-up location is the driver assigned to the ride by the on-demand scheduling and service system. A similar interface can be provided for the driver to scan and verify the fingerprints of the rider, a person supervising the rider at the pick-up location, a person receiving the rider at the drop-off location, or another person associated with the rider.

In some examples, the system can generate a unique visual code and provide the code to both the driver and the user. Matching of the driver's code to the user's code can help the user to confirm that the driver is the driver assigned to the user's ride and can help the driver to confirm that the rider is the person to whom the driver is assigned. In some examples, the visual code can be a pattern of colors that can be compared visually, e.g., by the driver, the user, or the rider. In some examples, the visual code can be a scannable code, such as a bar code or a QR code, that can be scanned by a device (e.g., the driver's device) and matched by an automated determination.

Figure 13:
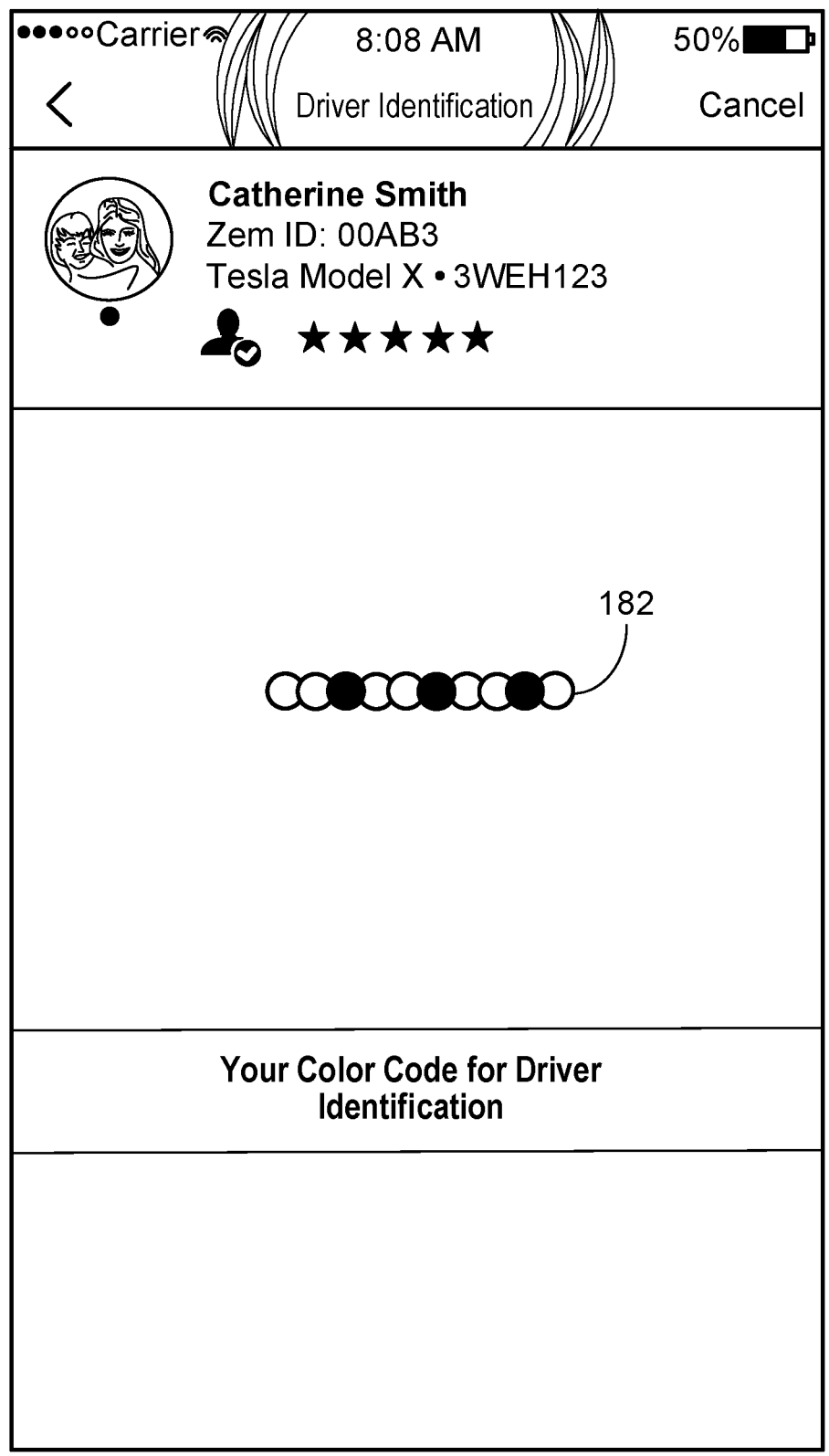

Referring to FIG. 13, in an example, the visual code can be displayed as a one-dimensional pattern 182 of colored dots on the user interface of the user's mobile device. In some examples, the same pattern of colored dots can be displayed on the user interface of the driver's mobile device, and a match between the driver's pattern and the user's pattern can act as a verification of the identity of both the driver and the user. In some examples, multiple lights, such as light emitting diodes (LEDs) can be installed in or on the driver's vehicle, such as on the roof or the front or rear windshield or elsewhere on the vehicle. The lights installed on the driver's car can be lit in the same pattern as the pattern 182 of colored dots displayed on the user's user interface, enabling the user to identify the driver's vehicle. Displaying the visual code in lights on the driver's vehicle can also help the user to find the driver if the pick-up location is crowded or dark.

In some examples, the visual code can be a static code that does not change. In some examples, the visual code can be a dynamic code that changes with time. The changes in the visual code can occur concurrently in the pattern 182 on the user's user interface and in the pattern displayed on the driver's user interface or the driver's vehicle. The visual code and/or the changes to a dynamic visual code can be randomly generated by the on-demand scheduling and service system 150.

The lights on the driver's vehicle can be solar powered or battery powered. The lights can have a communication component, such as a Bluetooth™ or a wireless sensor installed which can connect the lights with a program or application that is stored and operated on the driver's mobile device to receive the visual code. In some examples, ZigBee, Z-Wave or other such communication protocols can be used to connect the lights with the driver's device.

Figure 14:
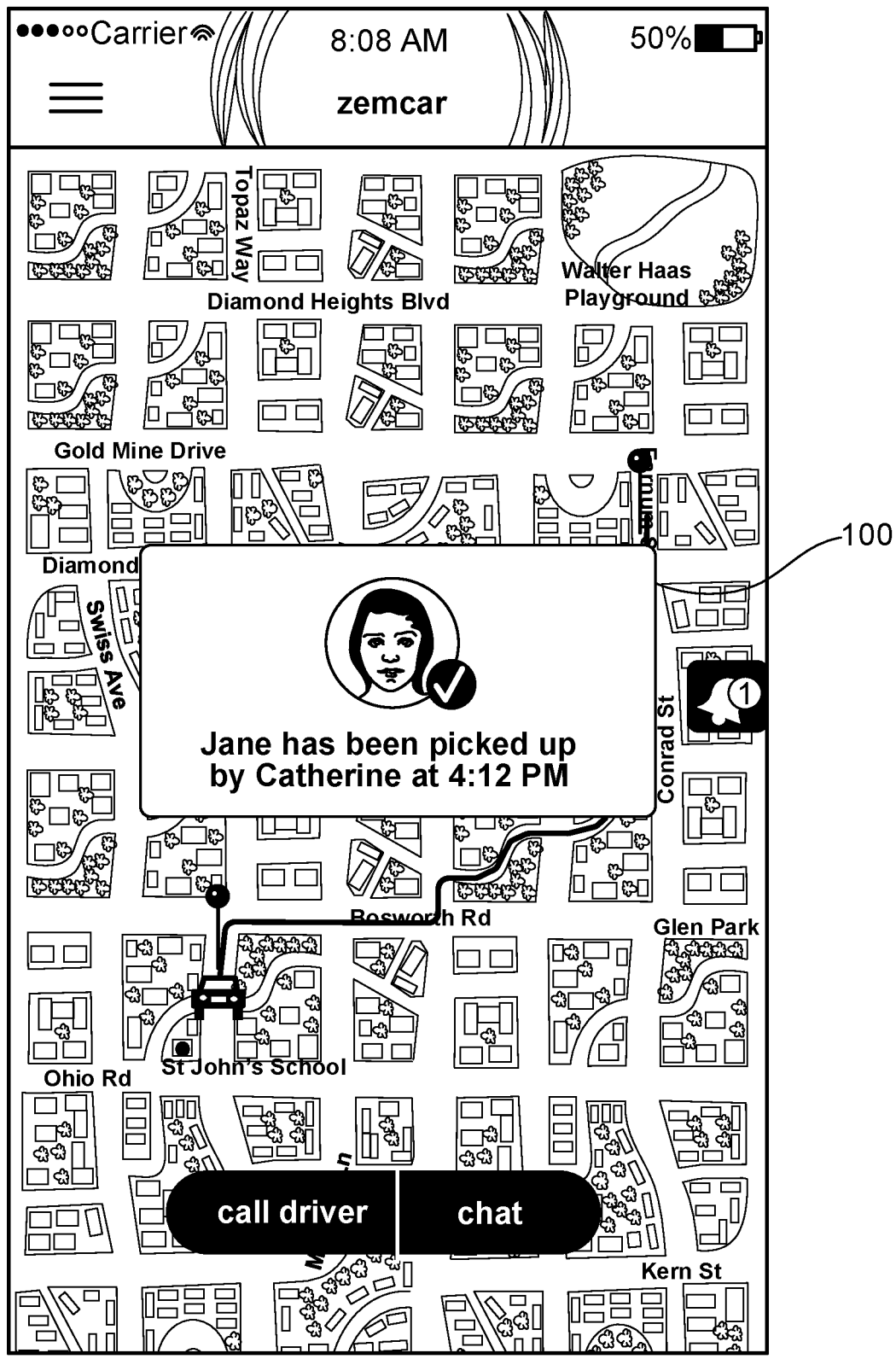

Referring to FIG. 14, once the driver has picked up the rider, a notification 100 can be sent to the user or to a supervisor of the rider. The driver's route can be tracked in real time on the user's mobile device. The user can be provided with the ability to call or chat with the driver.

In some examples, the driver's behavior can be monitored during the ride. Monitoring the driver's behavior can include monitoring driving behavior such as speed or acceleration (e.g., sudden acceleration or braking), monitoring the driver's use of his mobile device (e.g., whether the driver makes or takes calls, sends text messages, browses the internet, or other activities), or monitoring other types of data. Data indicative of the driver's behavior can be stored in a database of the on-demand scheduling and service system 150. The data indicative of the driver's behavior can be analyzed and used to determine a rating of the driver, such as a trustworthiness of the driver, that can be used, e.g., in determining the driver's trust barometer value.

In some examples, the driver's behavior can be controlled during the ride. Controlling the driver's behavior can include controlling the driver's driving behavior, such as preventing the driver from driving above a certain speed, preventing the driver from using sudden acceleration or braking, or preventing the driver from taking other actions. Controlling the driver's behavior can include controlling the driver's use of his mobile device, such as preventing the driver from making or taking calls, sending text messages, browsing the internet, or taking other actions. In some examples, the driver's behavior can be controlled according to default rules. In some examples, the user can define rules to be used to control the driver's behavior. For instance, a user may want to allow the driver to accept phone calls so that the user can call the driver to discuss the status of the rider, but may want to prevent the driver from using his mobile device in any other way.

In some examples, the status or behavior of the driver, the rider, or both can be monitoring by video and/or still images of the rider and/or driver. The video and/or still images can be transmitted in real-time or near real-time to the user or to another person. In some examples, the route of the ride can be tracked in real-time or near real-time and the tracking information transmitted to the user or to another person.

In some examples, when the ride begins, the on-demand and scheduling service system 150 begins capturing live video of the rider, e.g., through a camera hardware component of the driver's device or through a freestanding camera mounted in the driver's vehicle. The on-demand scheduling and service system facilitates broadcasting of the live video to the user or to another party, such as to an operations center of the on-demand and scheduling service system 150 and/or any to other individual designated by the user to watch the video streaming of the ride. For instance, the on-demand and scheduling service subsystem can implement one or more interfaces, e.g., a Web interface 128, a mobile application interface 102, or another type of interface, to broadcast live video of the ride and to enable tracking the route of the ride on a map 108. One or more of these interfaces can be made available to the user, to a customer support center, and/or to other individuals selected by the user to enable monitor his/her rider by watching live video streaming. Video data of the ride is processed through an internal communication interface 34 according to application rules 22 and sent to the on-demand and scheduling service system 150 through a network interface 38 of the client device 54 of the driver. A data creator component 42 can be operated to store the video data in the functional database 48 of the on-demand and scheduling service system 150. A video broadcasting manager 110 uses the data retriever 50 component of the data access controller 40 to broadcast the live video of rider according to application rules 22. A user interaction manager 12 enables the user and/or other individuals designated by the user to watch live video streaming of rider in one or more client devices 54. The video of the rider recorded during the ride can be stored in the functional database 48 of the on-demand and scheduling service system 150 and can be utilized in situations like accidents and other emergencies, or can be streamed but not stored, or both.

Figure 15:
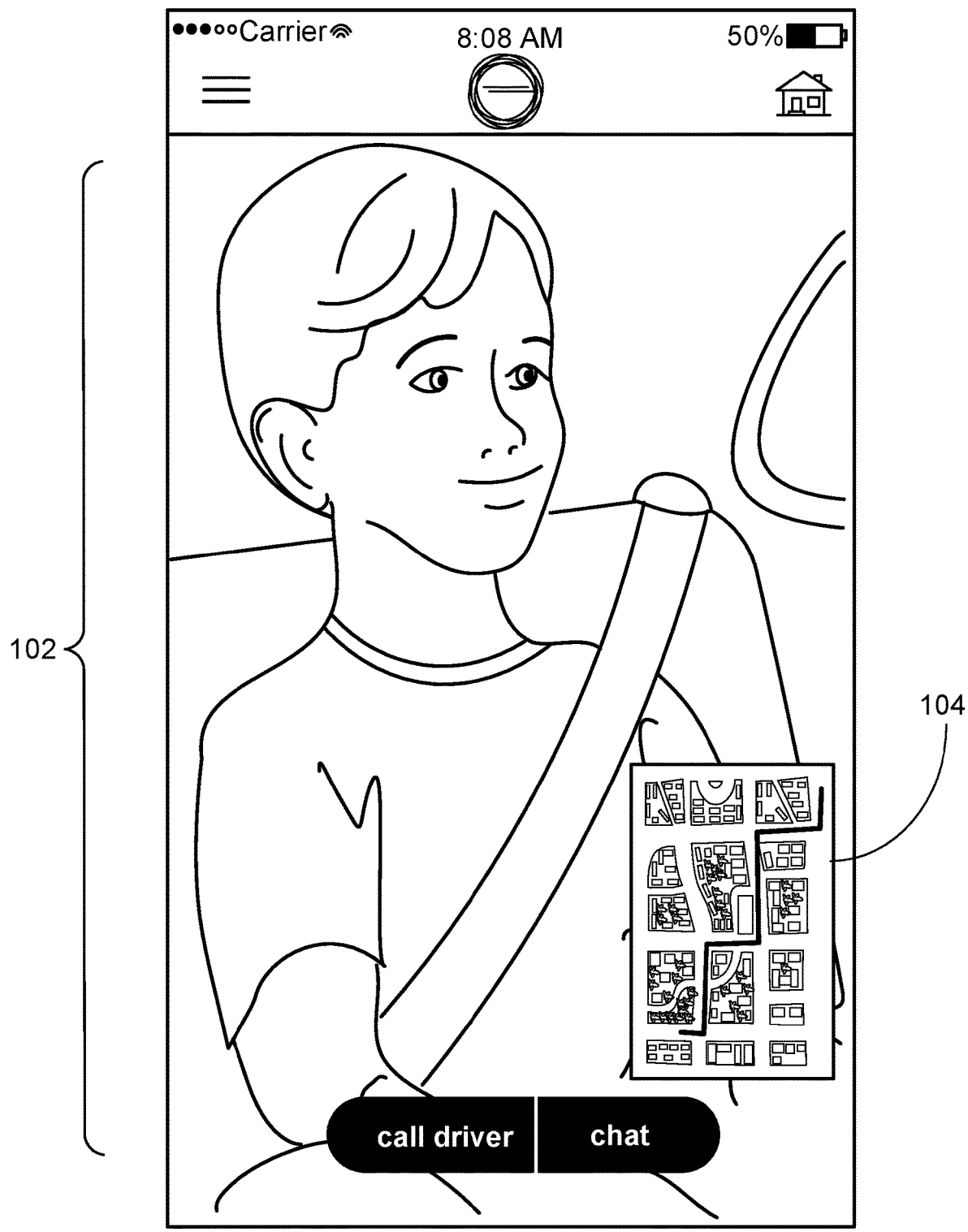
Figure 16:
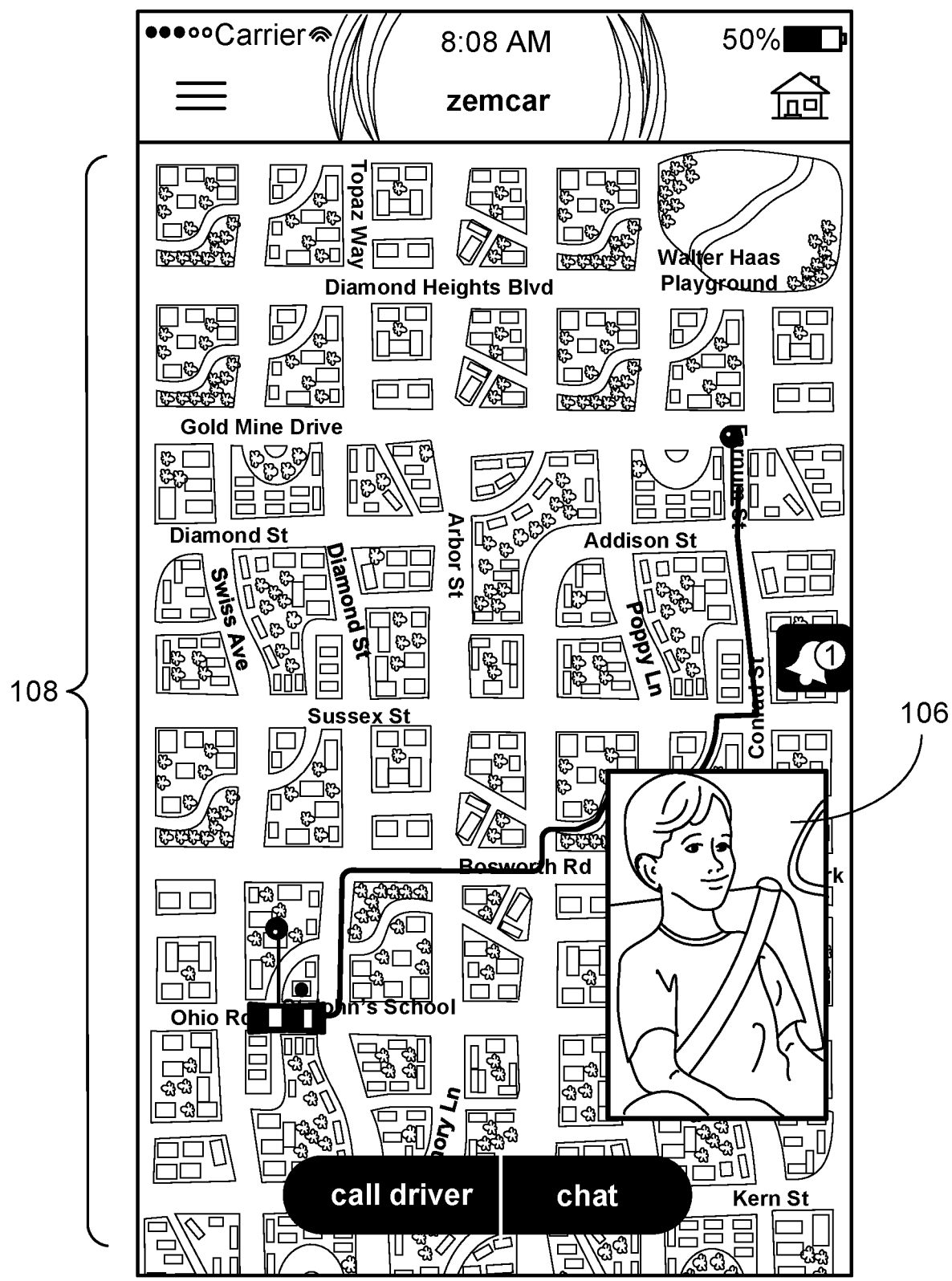
Figure 17:
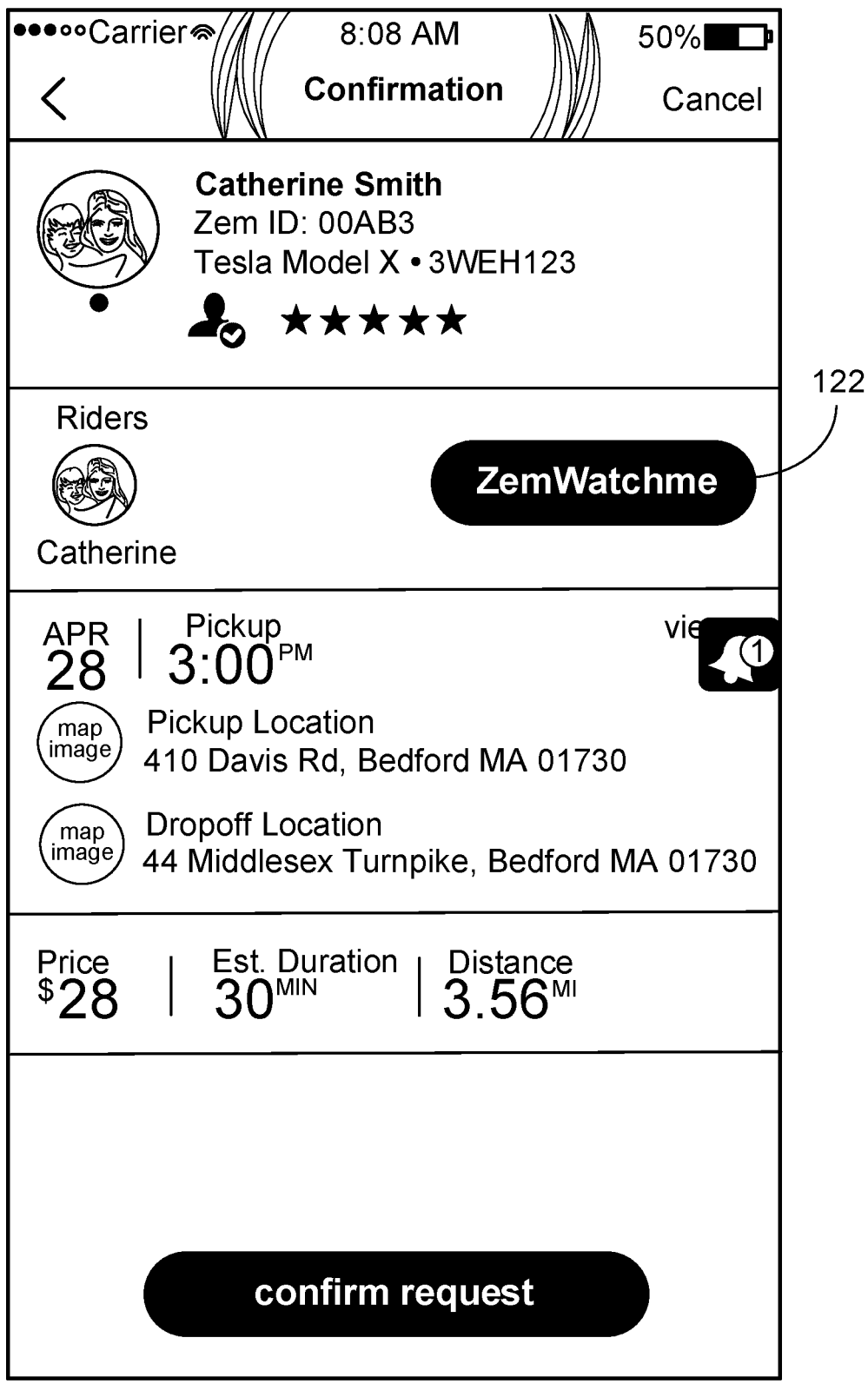

Referring to FIG. 15, an example interface 102 shows streaming live video of the rider during a ride. A map 104 inset into the video screen displays the predicted route and the current location of the driver's vehicle. The interface 102 can include controls for contacting the driver. Referring to FIG. 16, in another example interface 104, the map 104 is the primary display and a smaller video 106 showing a live stream of the rider during the ride is displayed as an inset into the map 104. Referring to FIG. 17, in some examples, the driver can enable live video streaming using a control 122.

Figure 18:
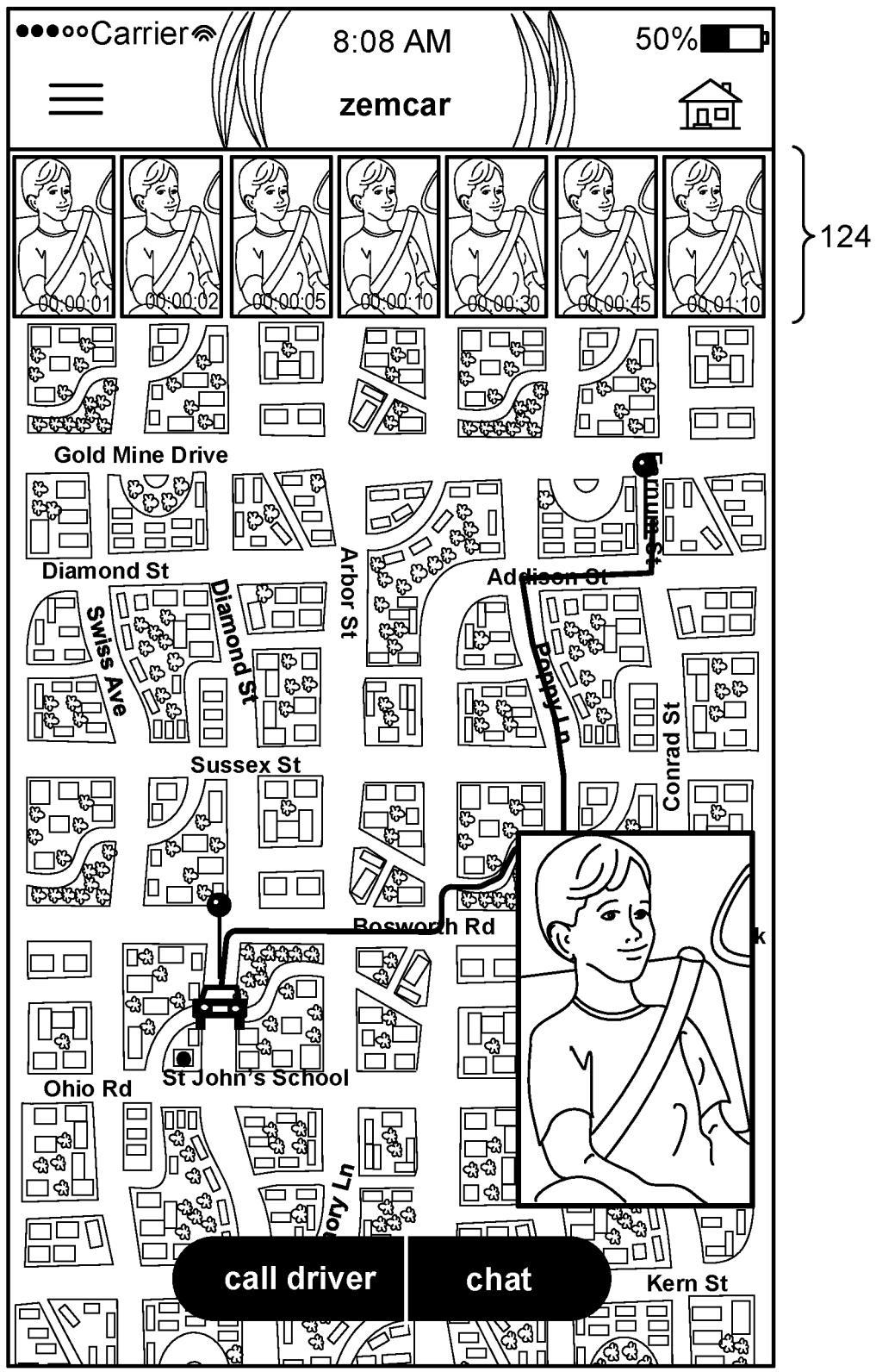

Referring to FIG. 18, in some examples, the status or behavior of the rider and/or the driver can be monitored through one or more still images 124. For instance, a picture or bursts of multiple pictures of the rider during the ride can be captured at various points during the ride, such as at regular or random intervals. The pictures can be taken by an operating program or application on the client device 54 of the driver or can be taken by a separate camera, e.g., a camera installed in the driver's vehicle. The pictures or bursts of pictures can be streamed to the on-demand and scheduling service system 150 which can then stream the pictures or bursts of picture to the user or to other individuals designated by the user. The quality of pictures or streaming video can be controlled through resolution and can be upscaled and/or downscaled manually or automatically by the system, e.g., responsive to data storage, bandwidth, or data transmission limitations. A low resolution (e.g., 240*p* bit rate) can be used to provide sufficient view of the ride while using less data storage and consuming less bandwidth, thus making the broadcasting more cost effective and efficient.

In some examples, the on-demand and scheduling service system 150 can allow the user or the rider or both to choose a person, such as a friend or a family member, to monitor their ride in real time by watching the live video streaming, viewing the broadcasted pictures, tracking the ride on map, or monitoring in another way. Users have full control over who can watch and track the ride. When a user generates a ride request, one or more service options can be displayed by the on-demand and scheduling service system 150 so that the user can choose from service options and designate a person (e.g., someone they trust) to share the ride details with and to allow them to watch the live video of their ride. The on-demand and scheduling service system 150 can send a notification to the designated individual, such as to the designated individual's mobile computing device. The designated individual can start tracking the rider on a map and monitoring video streaming of the rider from the pickup location to the drop off location for on demand rides, scheduled rides, or both.

In some examples, the on-demand and scheduling service system 150 can provide functionality to enable the rider to generate a panic alert if a distress situation occurs. For instance, the on-demand and scheduling service system 150 enables a user (e.g., an adult user) to create a family password by using a program or application that is operated on his/her mobile computing device and share the family password within his/her family. This family password is stored in the on-demand and scheduling service system 150 and can be visible to the support team of the system. During the ride if any kind of distress situation occurs the rider can send a panic alert to a customer support team by pressing a button displayed in the program or application that is operated on the rider's mobile computing device. Upon receipt of a panic alert, the support team can call the rider and ask for the family password. If it is wrong, the support team may determine that the rider is in distress and inform a law enforcement agency.

Figure 19:
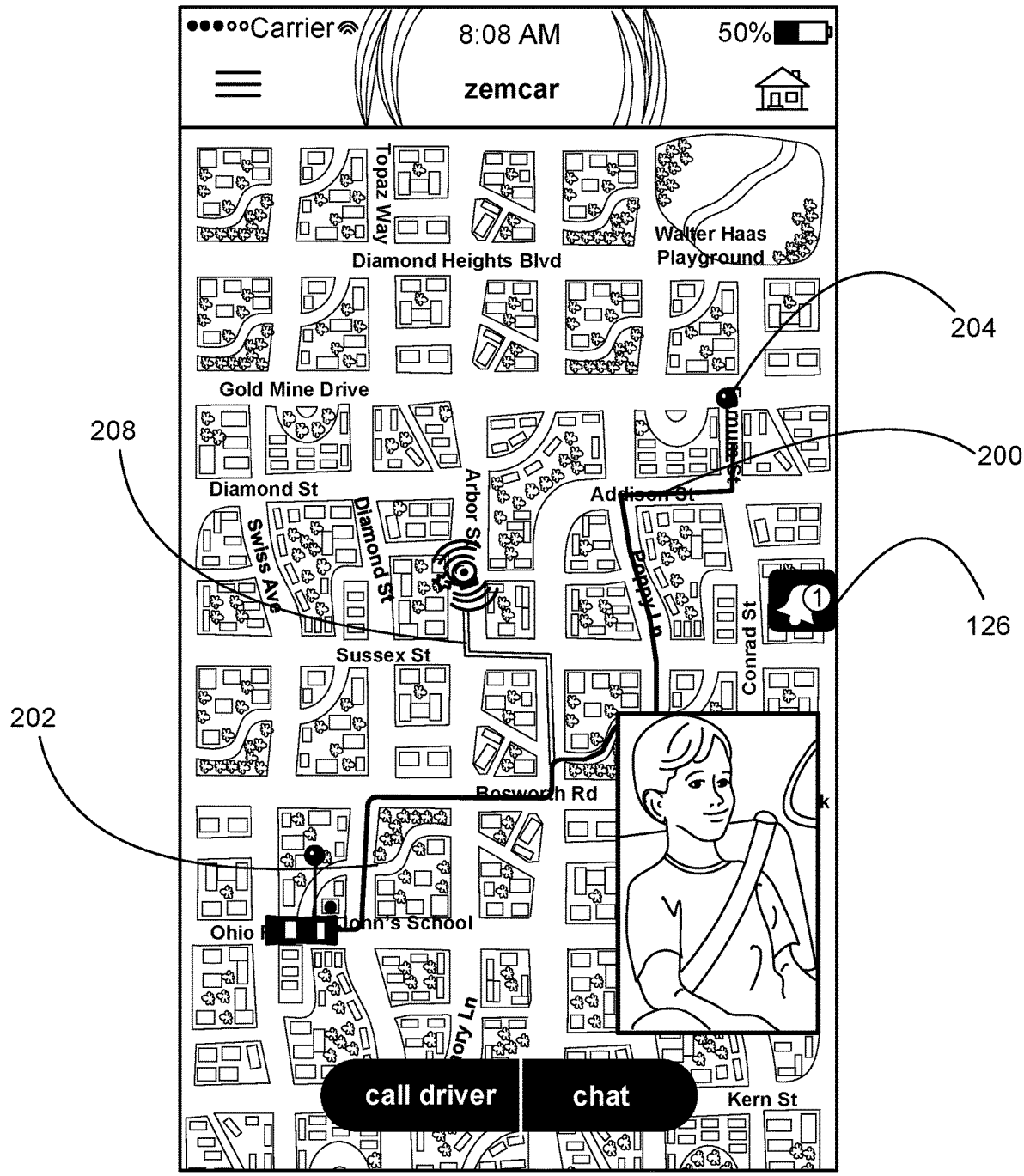

In some examples, the on-demand and scheduling service system 150 can provide geo-fencing functionality that generates an alert if the driver deviates from a prescribed route for a ride. Referring to FIG. 19, a suggested route 200 between a pick-up location 202 and a drop-off location 204 is shown. A configurable geo-fence can be created around the suggested route 200. If the driver crosses the geo-fence, e.g., by deviating too much from the suggested route 200, e.g., as shown by a deviation 208, an alert 126 is displayed to the user or to a third party monitoring the ride. The threshold deviation beyond which an alert is generated (e.g., the shape or radius of the geo-fence) can be adjusted according to one or more rules, e.g., specified by the user. For instance, rules can be defined to accommodate tolerance for longer routes, traffic, construction, or other occurrences likely to be encountered by a driver.

The alert can be a visual alert (e.g., using color coding), an audio alert, or another type of alert. A support team administering the on-demand scheduling and service system 150 can be alerted and can call the rider and/or the driver to request an explanation for the deviation. If the deviation from declared path is not legitimate, the support team can inform a law enforcement agency and provide the exact location of the vehicle.

Figure 20:
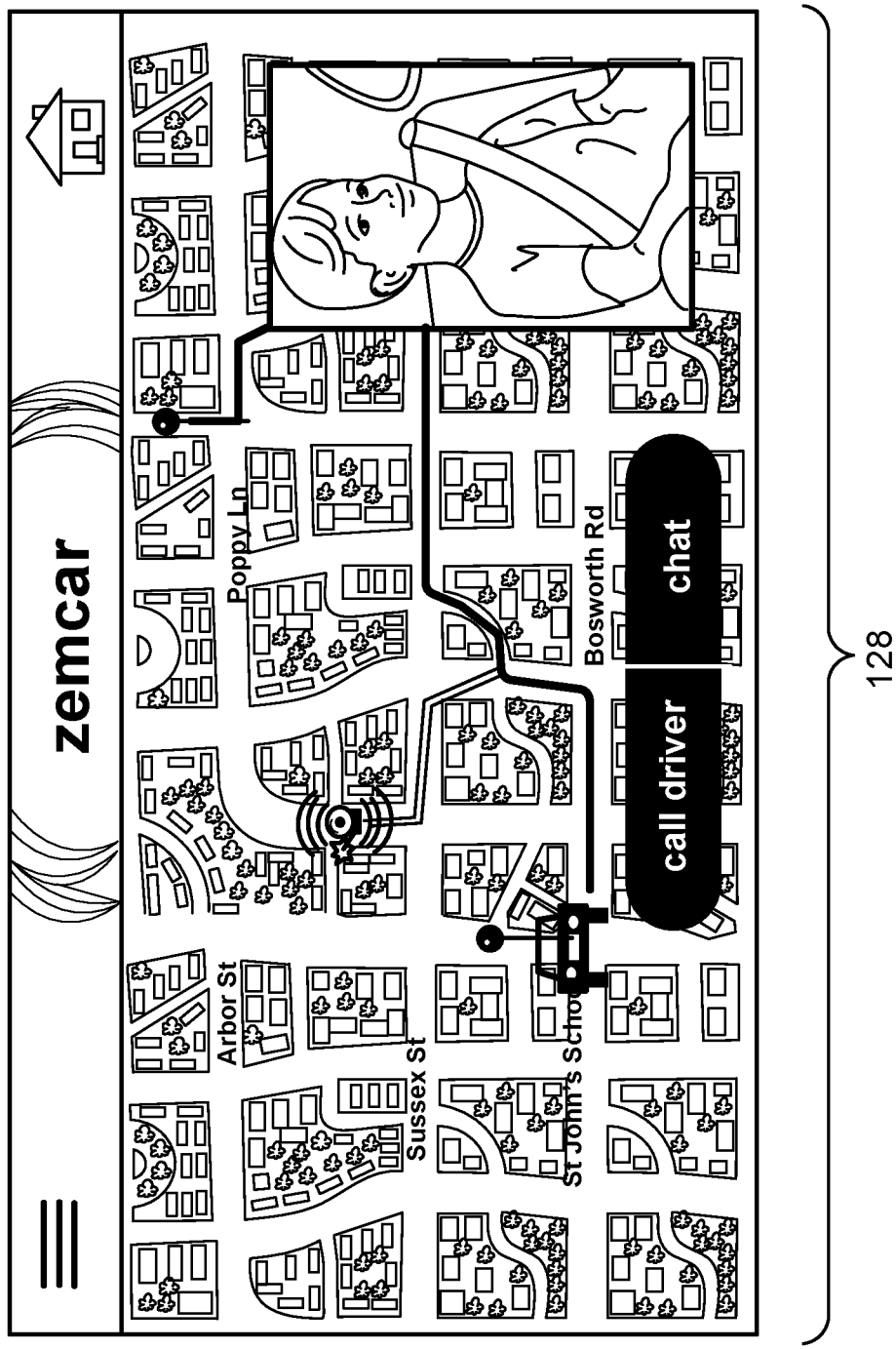

FIG. 20 shows an alternative view of a deviation from a suggested route and provides controls by which the user can contact the driver.

Figure 21:
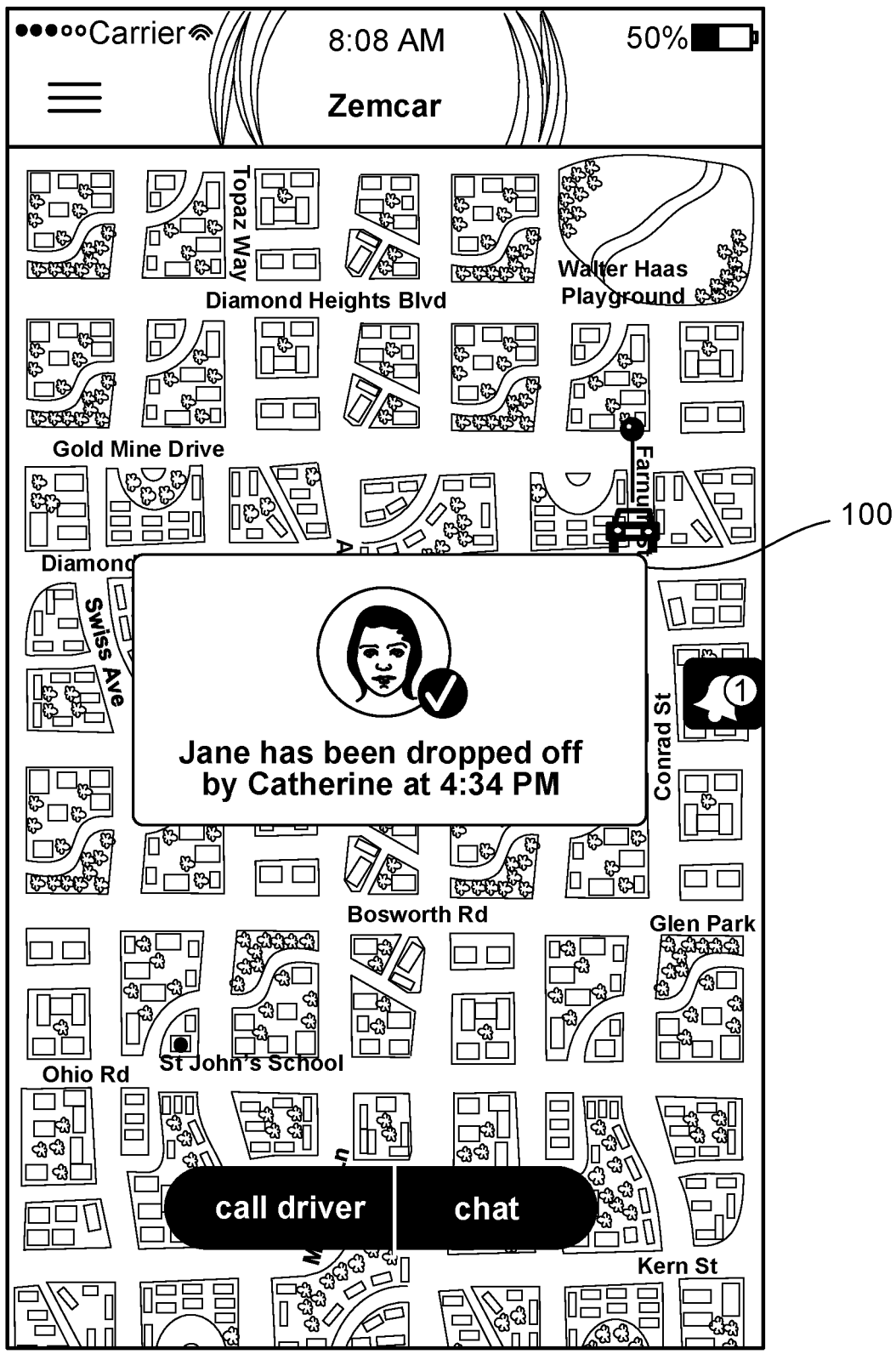

Referring to FIG. 21, when the rider is dropped off, a notification 110 can be provided to the user. The notification can include the time and image of the rider. In some examples, the notification can be initiated only after the rider has exited the driver's vehicle as confirmed by images, video, input from the rider, or other types of confirmation.

Figure 22:
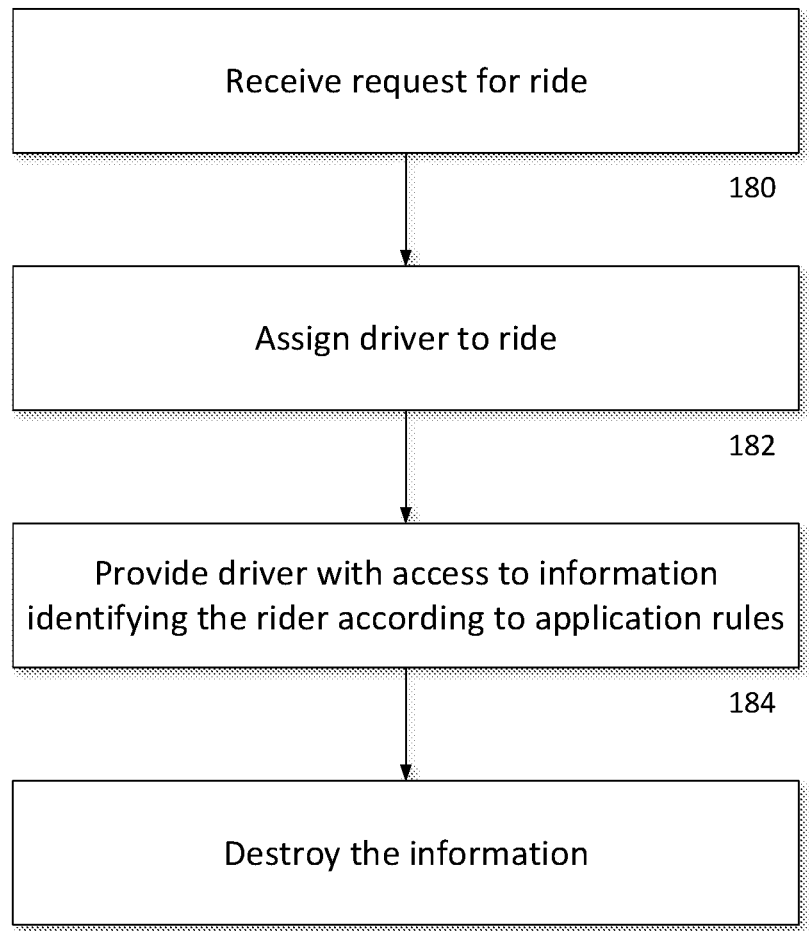
FIGS. 22 and 23 are flow charts.

Referring to FIG. 22, in an example process, a request for a ride is received from a user (180). A driver is assigned to provide the ride for the user (182), e.g., based on a trust the user has for the driver. The driver is provided with access to information uniquely identifying the user or a rider according to one or more application rules associated with the request for the ride (184). For instance, the driver can be provided with access to the information based on the location of the driver and/or for a limited period of time. The information can be destroyed according to one or more of the application rules (186).

Figure 23:
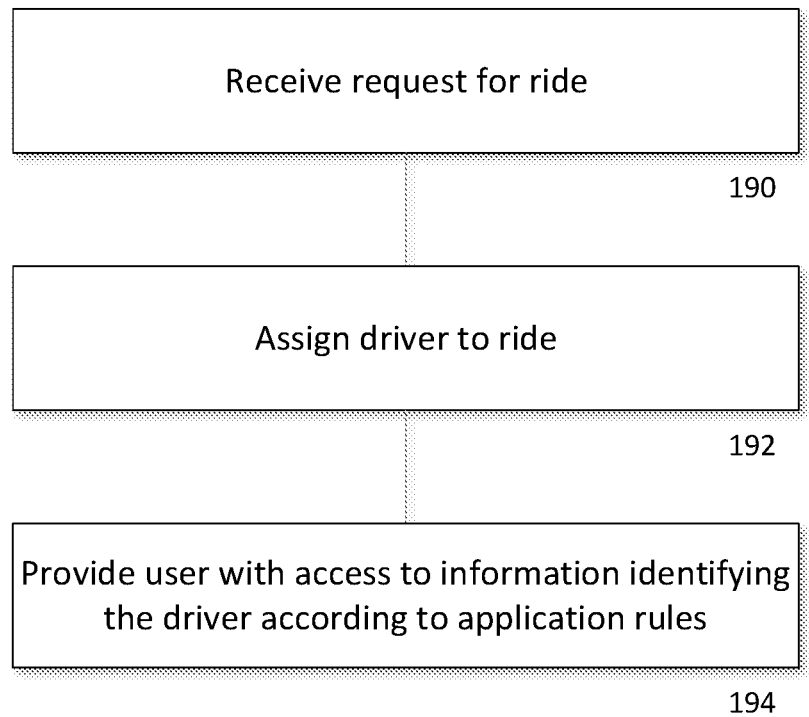

Referring to FIG. 23, in an example process, a request for a ride is received from a user (190). A driver is assigned to provide the ride for the user (192), e.g., based on a trust the user has for the driver. The user is provided with access to information uniquely identifying the driver according to one or more application rules associated with the request for the ride (194). For instance, the user can be provided with a visual code that can be matched with a visual code displayed on the driver's vehicle or mobile device.

Application rules 22 are a component of data processing logic of a program or application which controls the overall flow of data processing through the program or application. Application rules 22 are a formal expression of application functionality for a state of the application, and the application rules 22 determine how data can be created, stored, changed, accessed or displayed through an application or program in response to one or more inputs.

An example of an application rule can include the process for selecting a driver responsive to a user's request for ride. For instance, when the user sends a request for ride, the on-demand and scheduling service system 150 selects and assigns a trusted driver and forwards the user request to that driver. The selection of driver and the forwarding of the user's request to the selected driver is performed according to configurable application rules, such as rules specifying a threshold distance from the pick-up within which drivers available to be selected by the on-demand and scheduling service system 150 should be currently located. For instance, the on-demand and scheduling service system 150 may consider only those drivers currently located within a 3 mile radius of the pick-up location for selection.

An example of an application rule relates a process for enabling a driver to accept a user's request for ride. For instance, configurable application rules can specify a time threshold within which a selected driver is to accept the user's request for ride. For instance, when the system forwards the user's request for ride to a selected driver, the driver can accept this request according to configurable application rules. For example, the driver can only accept the request within 15 seconds after receiving it.

An example of an application rule relates to notifications to a user about a driver's estimated arrival time. When a driver accepts the user's request for ride and leaves for the pick-up location, the user is notified about the driver's estimate arrival time. These notifications are sent according to configurable application rules. For example, the on-demand and scheduling service system 150 notifies the user when the driver is estimated to be 10 minutes away and again when the driver is estimated to be 5 minutes away.

An example of an application rule relates to instructions or permissions. When a user requests a ride, the user can provide secure text, audio, video instructions/permissions for pick-up. Configurable application rules can specify criteria for these instructions or permissions, such as maximum file sizes, maximum durations, a maximum number of separate instructions, or other criteria. For instance, audio or video instructions can be recorded according to one or more configurable application rules specifying that the audio or video length can be no more than, e.g., 10, 15, or 20 seconds.

An example of an application rule relates to driver viewing of instructions or permissions. Configurable application rules can specify criteria related to where the driver is allowed to view the instructions or permissions, the number of times the driver is allowed to view the instructions or permissions, the amount of time the driver is allowed to spend viewing the instructions or permissions, or other criteria. For instance, an application rule may specify that the driver can only view the instruction or permissions after reaching the pick-up location. For instance, the application rule may specify that the driver can view the instructions only once and for a maximum interaction time of 20 seconds.

Figure 24:
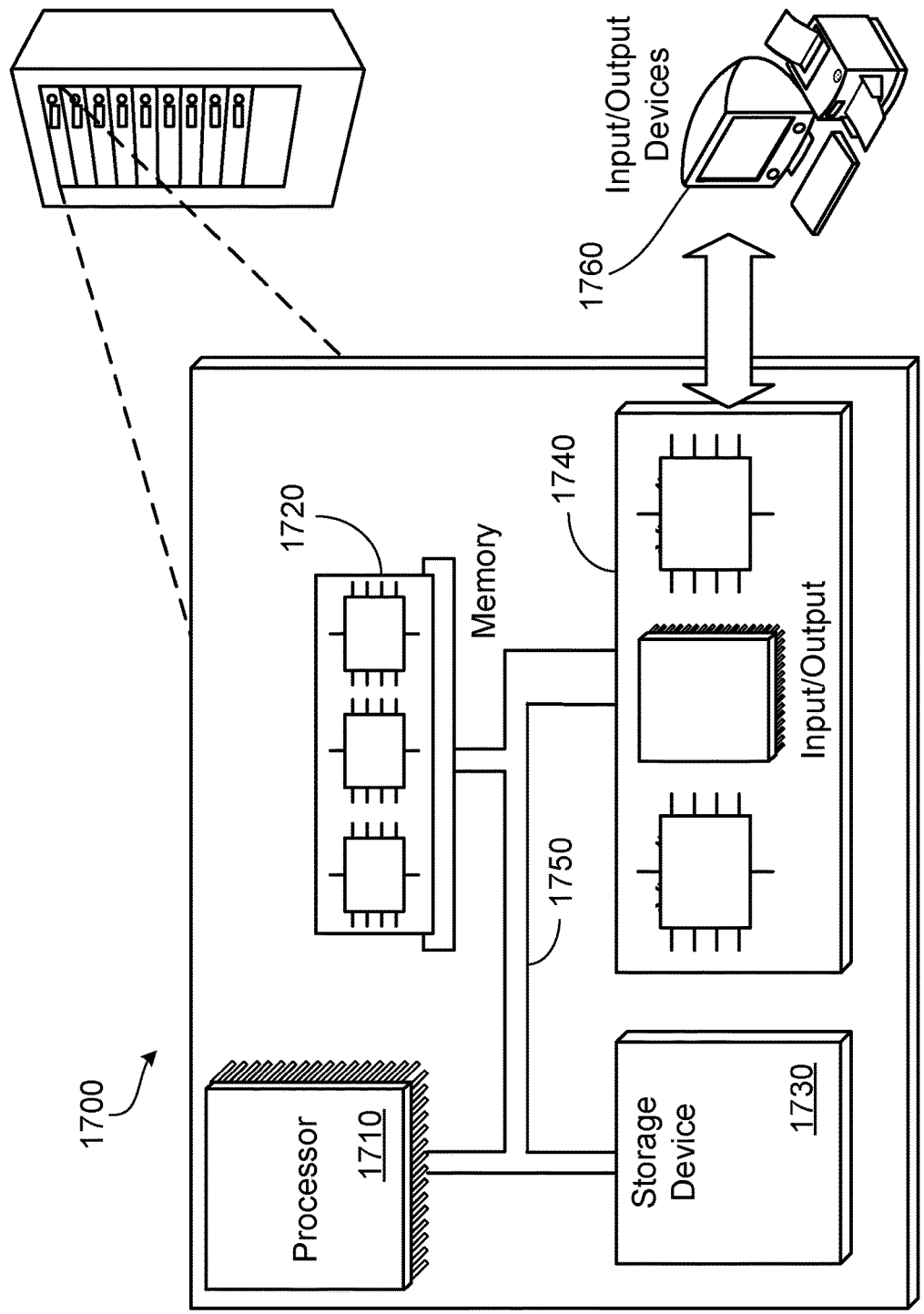
FIG. 24 is a diagram of a computing system.

FIG. 24 is a block diagram of an example computer system 1700 that may be used in implementing the technology described in this document. General-purpose computers, network appliances, mobile devices, or other electronic systems associated with the users may also include at least portions of the system 1700. The system 1700 includes a processor 1710, a memory 1720, a storage device 1730, and an input/output device 1740. Each of the components 1710, 1720, 1730, and 1740 may be interconnected, for example, using a system bus 1750. The processor 1710 is capable of processing instructions for execution within the system 1700. In some examples, the processor 1710 is a single-threaded processor. In some examples, the processor 1710 is a multi-threaded processor. The processor 1710 is capable of processing instructions stored in the memory 1720 or on the storage device 1730.

The memory 1720 stores information within the system 1700. In some examples, the memory 1720 is a non-transitory computer-readable medium. In some examples, the memory 1720 is a volatile memory unit. In some examples, the memory 1720 is a non-volatile memory unit.

The storage device 1730 is capable of providing mass storage for the system 1700. In some examples, the storage device 1730 is a non-transitory computer-readable medium. In various different examples, the storage device 1730 may include, for example, a hard disk device, an optical disk device, a solid-date drive, a flash drive, or some other large capacity storage device. The input/output device 1740 provides input/output operations for the system 1700. In some examples, the input/output device 1740 may include one or more of a network interface devices, e.g., an Ethernet card, a serial communication device, e.g., an RS-232 port, and/or a wireless interface device, e.g., an 802.11 card, a 3G wireless modem, or a 4G wireless modem. In some examples, the input/output device may include driver devices configured to receive input data and send output data to other input/output devices, e.g., keyboard, printer and display devices 1760. In some examples, mobile computing devices, mobile communication devices, and other devices may be used.

In some examples, at least a portion on-demand and scheduling service system 150 can be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 1730 may be implemented in a distributed way over a network, such as a server farm or a set of widely distributed servers, or may be implemented in a single computing device.

Although an example processing system has been described in FIG. 21, examples of the subject matter and the functional operations described above may be implemented in other types of digital electronic circuitry, or in computer software, firmware, or hardware, including the structures disclosed in this specification and their structural equivalents, or in combinations of one or more of them. Examples of the subject matter described in this specification may be implemented as one or more computer program products, i.e., one or more modules of computer program instructions encoded on a tangible program carrier, for example a non-transitory computer-readable medium, for execution by, or to control the operation of, a processing system. The non-transitory computer readable medium may be a machine readable storage device, a machine readable storage substrate, a memory device, a composition of matter effecting a machine readable propagated signal, or a combination of one or more of them.

The term "system" may encompass all apparatus, devices, and machines for processing data, including by way of example a programmable processor, a computer, or multiple processors or computers. A processing system may include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) may be written in any form of programming language, including compiled or interpreted languages, or declarative or procedural languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD ROM disks. The processor and the memory may be supplemented by, or incorporated in, special purpose logic circuitry. Computers used in the system may be general purpose computers including mobile devices, custom-tailored special purpose electronic devices, or combinations of the two.

Examples may include a back end component, e.g., a data server, or a middleware component, e.g., an application server, or a front end component, e.g., a client computer having a graphical user interface or a Web browser through which a user may interact with an example of the subject matter described is this specification, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

Certain features that are described above in the context of separate examples may also be implemented in combination in a single example. Conversely, features that are described in the context of a single example may be implemented in multiple examples separately or in any sub-combinations.

The order in which operations are performed as described above may be altered. In certain circumstances, multitasking and parallel processing may be advantageous. The separation of system components in the examples described above should not be understood as requiring such separation.

It is contemplated for embodiments described herein to extend to individual elements and concepts described herein, independently of other concepts, ideas or system, as well as for embodiments to include combinations of elements recited anywhere in this application. Present embodiments are described here in detail with reference to the accompanying drawings, and the on-demand and scheduling service system 150 is not limited to these particular embodiments. The on-demand and scheduling service system 150 has been described in terms of particular embodiments and applications, and preceding description contains significant details. It should not be interpreted as limiting the scope of the on-demand and scheduling service system 150 but rather as providing illustrations of the preferred embodiments of the on-demand and scheduling service system 150, and it will be understood that many substitutions, changes and variations in the described embodiments, applications and details of the method and system illustrated herein and of their operation can be made by those skilled in the art without departing from the spirit of this description.

Other implementations are also within the scope of the following claims.

What is claimed is:

1. A method comprising:
   during transportation of a rider in a vehicle by a driver in a ride arranged by a computer-implemented driver assignment platform:
   receiving data designating a computing device of a supervisor of the rider for the computer-implemented driver assignment platform, the designating having been based on a relationship between the supervisor and the user;
   in response to receiving the data designating the computing device of the supervisor, permitting the computing device of the supervisor to receive an image of the rider representing transportation of the rider in the vehicle for the ride;
   determining a bandwidth limitation for transmitting data between the computer-implemented driver assignment platform and one or more of a computing device associated with the vehicle and the computing device associated with the supervisor of the rider;
   causing adjustment of a resolution of the image of the rider based on the determined bandwidth limitation;
   enabling transmission of (i) the image of the rider, (ii) data indicative of a map depicting a predicted route of the ride arranged by the computer-implemented driver assignment platform, and (iii) data indicative of an approximate location of the rider on the map in relation to the depiction of the predicted route, the approximate location corresponding where the rider is located on the map when the image of the rider is captured, from the computing device associated with the vehicle to the computer-implemented driver assignment platform and from the computer-implemented driver assignment platform to the computing device associated with the supervisor of the rider; and
   enabling transmission of control data, during transportation of the rider, from the computing device associated with the vehicle to the computing device associated with the supervisor of the rider, the control data indicative of a control button for a user interface of the device associated with the supervisor, the control button enabling the supervisor to initiate contact with the driver,
      wherein the image of the rider is configured to be displayed as an inset of the map depicting the predicted route of the ride, and wherein the approximate location of the rider when the image of the rider is captured is configured to be displayed on the map, and
      wherein the image of the rider, the control button, and the map are configured to be displayed concurrently on the user interface of the computing device associated with the supervisor during transportation of the rider;
   detecting that the transportation of the rider by the driver is completed; and
   in response to detecting that the transportation of the rider by the driver is completed, causing destruction of the image of the rider from one or more of the computer-implemented driver assignment platform, the device associated with the supervisor of the rider, and the computing device associated with the vehicle.

2. The method of claim 1, wherein enabling the image of the rider to be transmitted comprises streaming a live video of the rider.

3. The method of claim 2, comprising adjusting a bandwidth of the streaming video by upscaling or downscaling of video during live video streaming.

4. The method of claim 1, wherein enabling the image of the rider to be transmitted comprises controlling a camera in the vehicle to capture pictures or bursts of pictures of the rider and the car and enabling transmission of the pictures or the bursts of pictures.

5. The method of claim 1, wherein the map depicting the predicted route of the ride is configured to be displayed as an inset to the image of the rider.

6. The method of claim 1, comprising preventing one or more functions of the computing device associated with the vehicle from being operational during the ride in response to receiving a designation of the one or more functions of the device via one or more controls of the computer-implemented driver assignment platform.

7. The method of claim 1, comprising:
enabling the rider to generate a panic alert, using a rider device, responsive to a distress situation occurring during the ride; and
causing data to be transmitted to the rider in response to receiving the panic alert.

8. The method of claim 1, wherein causing adjustment of the resolution of the image enables real-time or near real-time transmission of the image.

9. The method of claim 1, wherein the computing device associated with the vehicle comprises a computing system of the vehicle.

10. The method of claim 1, wherein the computing device associated with the vehicle comprises a computing device of the driver.

11. The method of claim 1, further comprising:
receiving an image from the computing device associated with the vehicle;
determining that the rider is not present within the vehicle;
sending a notification to the computing device associated with the supervisor of the rider indicating that the rider is not present within the vehicle.

12. The method of claim 1, further comprising:
receiving a designation of a trusted client device via a user interface of the computer-implemented driver assignment platform; and
enabling transmission of the image to the trusted client device.

13. The method of claim 1, wherein the map depicts a drop-off location and a pick-up location of the rider.

14. The method of claim 1, wherein the image of the rider comprises a portion of a video stream, and wherein the approximate location of the rider is updated in approximately real-time.

15. The method of claim 1, further comprising enabling transmission of data, from the computing device associated with the vehicle to the computing device associated with the supervisor of the rider, the data indicative of a control configured to enable the supervisor of the rider to initiate transmission of the image of the rider and the data indicative of the map depicting the predicted route.

16. The method of claim 1, further comprising enabling transmission of data, from the computing device associated with the vehicle to the computing device associated with the supervisor of the rider, the data comprising an alert that the driver has deviated from the predicted route, the alert comprising a control for contacting the driver.

17. The method of claim 1, further comprising receiving data indicative of a geo-fence around the predicted route, wherein an alert that the driver has deviated from the predicted route is transmitted in response to the detecting that the rider has crossed the geo-fence.

18. The method of claim 1, wherein detecting that the transportation of the rider by the driver is completed comprises receiving an image indicating that the rider has exited the vehicle.

19. The method of claim 1, further comprising, during transportation of a rider in a vehicle by a driver in a ride arranged by a computer-implemented driver assignment platform, restricting a function of the computing device associated with the vehicle, the function including one or more of placing calls, sending a text message, and using a web browser.

20. The method of claim 1, wherein the relationship of the driver to the user is based on a trust of the driver by the user, the trust being based on one or more metrics of trust including one or more of a circle of trust for the user and a trust barometer value.

* * * * *